United States Patent [19]
Iijima

[11] Patent Number: 5,132,504
[45] Date of Patent: Jul. 21, 1992

[54] METHOD AND APPARATUS FOR STERILIZING SEALED CONTAINERS UTILIZING MICROWAVE

[75] Inventor: Kenichi Iijima, Isezaki, Japan

[73] Assignee: Eisai Co., Ltd., Tokyo, Japan

[21] Appl. No.: 530,414

[22] Filed: May 30, 1990

[30] Foreign Application Priority Data

Jun. 9, 1989 [JP] Japan .................................. 1-147666

[51] Int. Cl.⁵ .......................... A61L 2/12; H05B 6/78
[52] U.S. Cl. ..................... 219/10.55 A; 219/10.55 M; 219/10.55 F; 219/10.55 R; 422/21
[58] Field of Search ......... 219/10.55 A, 388, 10.55 F, 219/10.55 R; 422/21, 25, 292, 301, 302, 303, 304; 198/725, 730, 735.1, 733

[56] References Cited

U.S. PATENT DOCUMENTS

| | | | |
|---|---|---|---|
| 1,786,779 | 12/1930 | Quick | 198/725 |
| 2,912,093 | 11/1959 | Lauck | 198/733 |
| 3,778,964 | 12/1973 | Rowland | 219/388 |
| 3,885,915 | 5/1975 | Utsumi et al. | 219/550 |
| 4,091,726 | 5/1978 | Walker | 198/394 |
| 4,401,873 | 8/1983 | Berggren et al. | 219/10.55 A |
| 4,405,850 | 9/1983 | Edgar | 219/10.55 A |
| 4,420,982 | 1/1969 | Hager | 219/388 |
| 4,687,895 | 8/1987 | Chitre et al. | 219/10.55 A |
| 4,889,966 | 12/1989 | Meredith | 219/10.55 F |
| 4,940,865 | 7/1981 | Johnson et al. | 219/10.55 A |
| 5,061,443 | 10/1991 | Iijima et al. | 422/21 |

*Primary Examiner*—Bruce A. Reynolds
*Assistant Examiner*—Tuan Vinh To
*Attorney, Agent, or Firm*—Griffin, Branigan & Butler

[57] ABSTRACT

An irradiator furnace is connected to a square waveguide for propagation of microwaves and provided through a top wall with a slot. A conveyor bucket conveys sealed containers along the slot with lower portions of the sealed containers being inserted through the slot into the irradiator furnace. The irradiator furnace includes therein a rail which extends from a lower level of the furnace thereof at the inlet thereof to a higher level of the furnace at the outlet so as to support the sealed containers in a vertical direction. A hot air furnace is provided above the irradiator furnace. A narrow passage extending from the outlet of the irradiator furnace is directly followed by a thermostatic station utilizing an IR heater. So the sealed containers are sterilized.

12 Claims, 22 Drawing Sheets

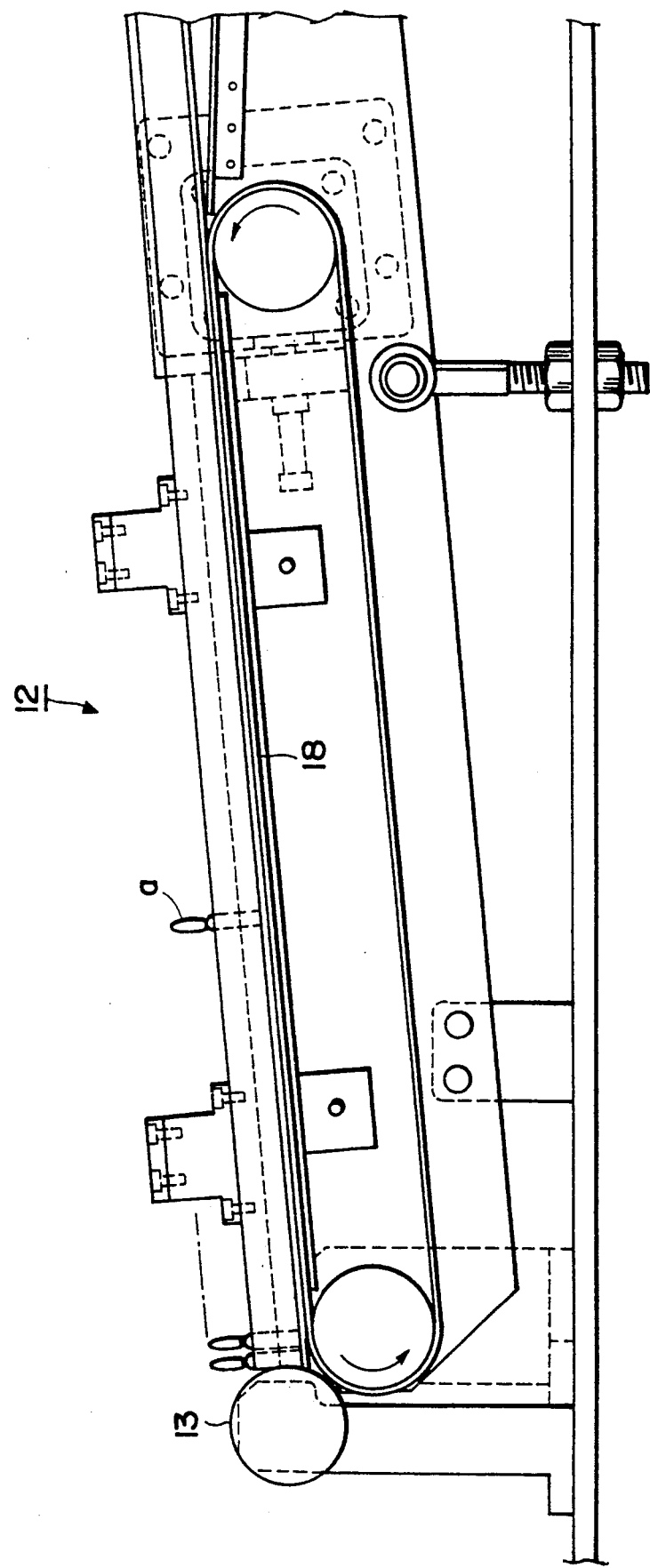

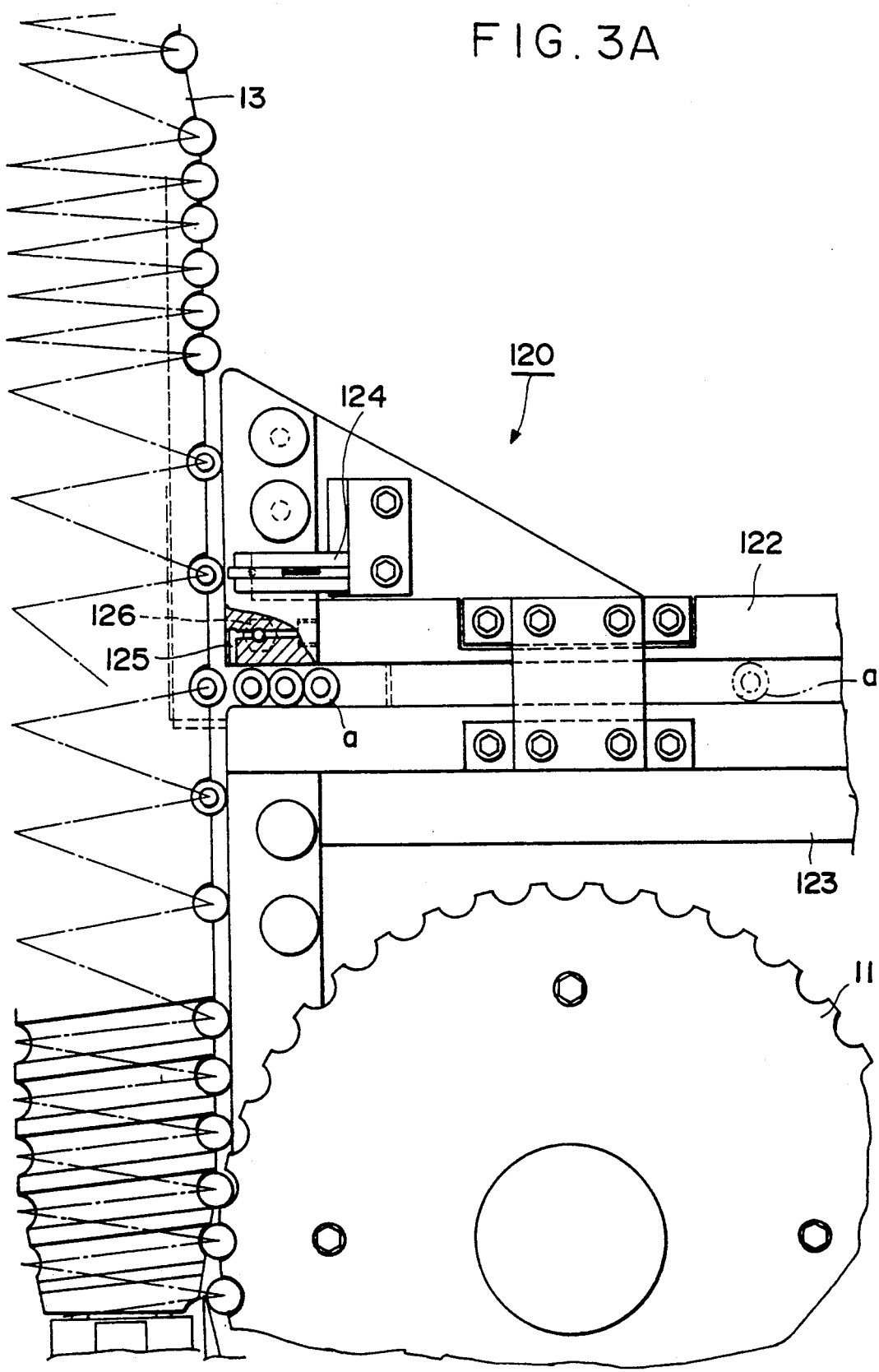

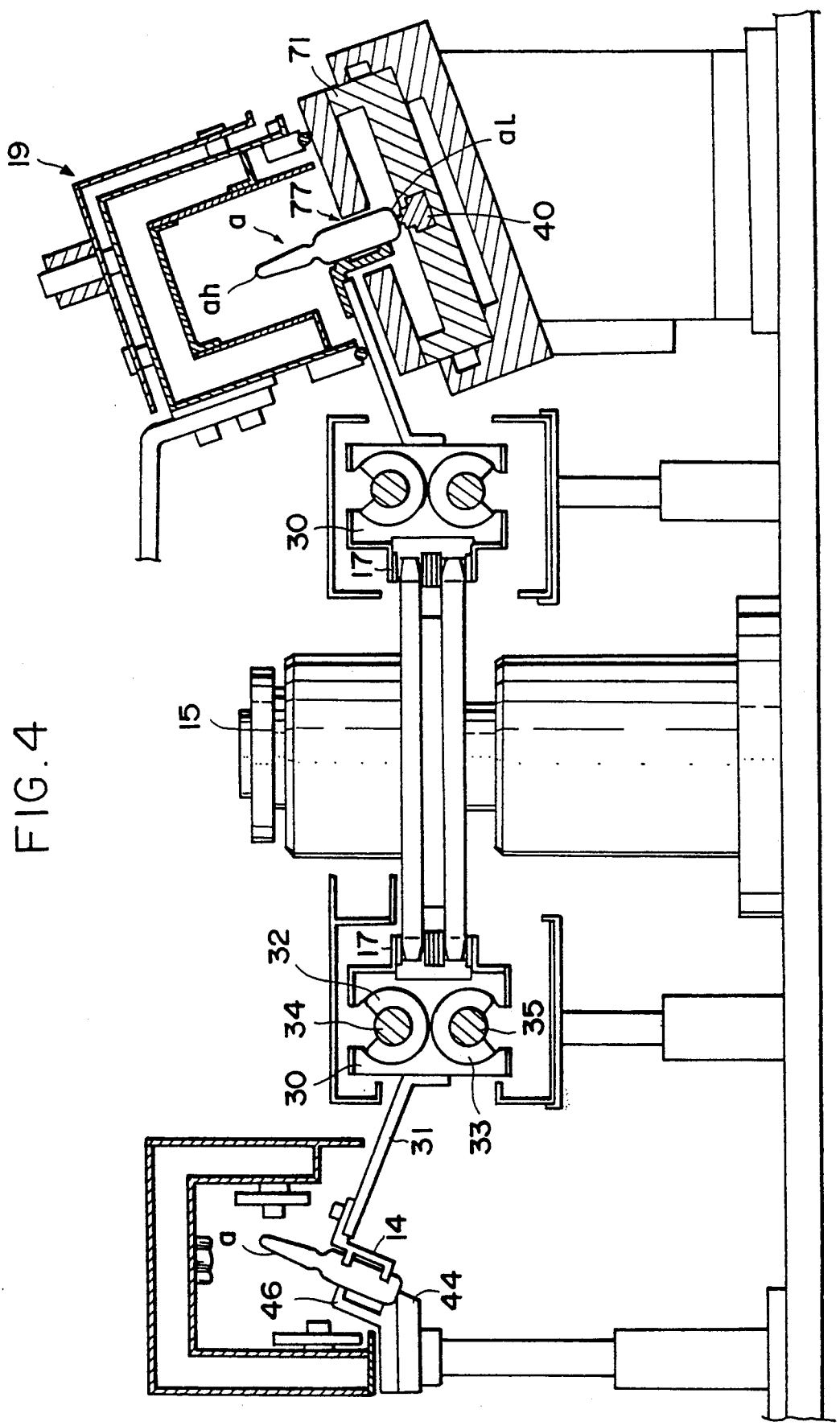

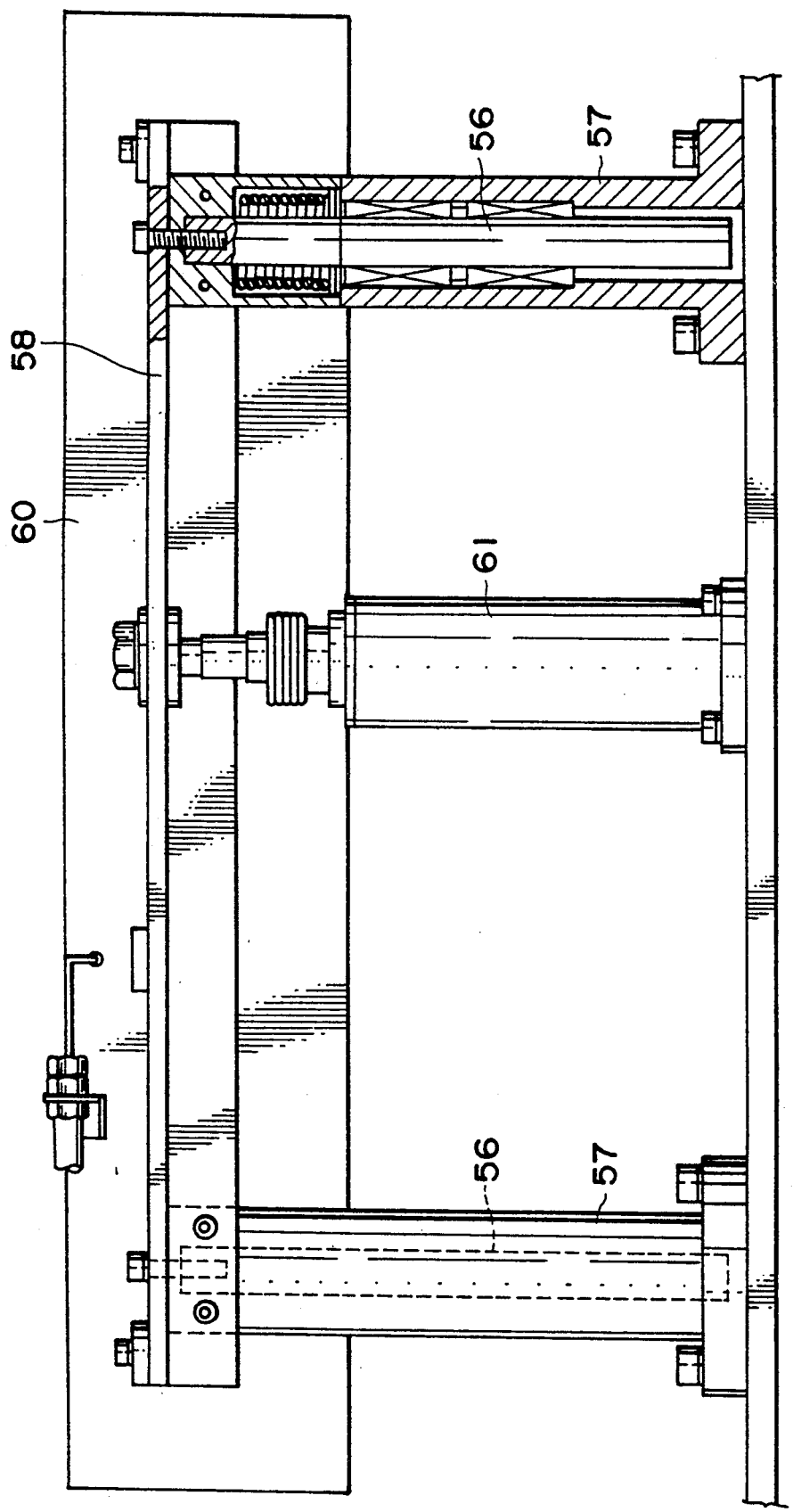

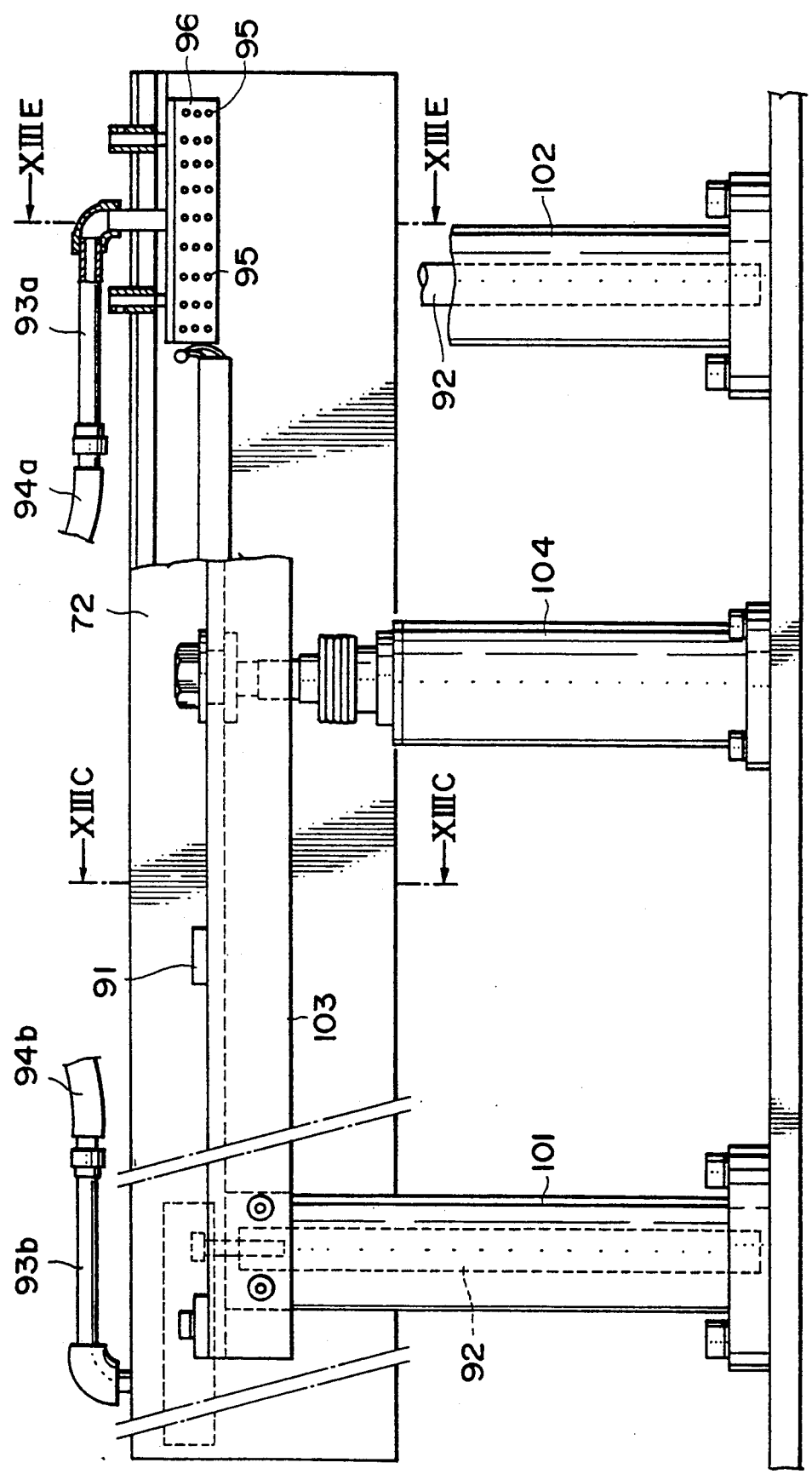

METHOD AND APPARATUS FOR STERILIZING SEALED CONTAINERS UTILIZING MICROWAVE

BACKGROUND OF THE INVENTION

The present invention relates to a method and an apparatus for heat-sterilizing sealed containers filled with medical fluid by exposing the sealed containers moving along a slot formed through atop wall of an irradiator furnace to microwave irradiated from a square waveguide connected to the irradiator furnace into the latter.

It is commonly adopted to practice to sterilize the sealed container, e.g., the ampule filled with medical fluid particularly for infection during a process of manufacturing.

To realize such sterilizing treatment, various apparatuses utilizing microwave or auto clave have conventionally been employed.

Among them, the apparatuses utilizing microwave are disclosed, for example, in Japanese Patent Application Disclosure Gazettes No. 1973-59976 "Method and apparatus for sterilization of medical fluid contained in ampule", No. 1973-104381 "method and apparatus for ampule filled with medical fluid", and No. 1975-38985 "Apparatus for sterilization of ampule filled with medical fluid".

However, the methods and apparatuses of prior art utilizing microwave have been inevitable accompanied with a problem as follows. Specifically, an absorptivity for microwave generally depends on a conductivity of particular medial fluid and there are various ampules not only concerning their sizes but also concerning quantities of medical fluid with which these ampules are filled. Accordingly, if these ampules are irradiated with microwave under same conditions without proper consideration of such differences, the temperature rise ratio would be undesirably uneven depending on a particular kind of medical fluid and a particular size of the ampule.

None of the above-identified disclosures can accommodate different temperature rise ratio presented by different kind of medical fluid and, in consequence, these disclosures disadvantageously give rise to uneven sterilizing conditions.

According to the invention disclosed by the first mentioned Japanese Disclosure Gazette No. 1973-59976, a lower portion of each ampule standing upright is irradiated with microwave to minimize temperature difference within the ampule. However, a desired heating efficiency can not be achieved merely by irradiating the ampule with microwave unless a long heating furnace is additionally provided. Furthermore, this invention requires a relatively high microwave capacity and such requirement is another obstacle which makes an efficient sterilization impossible.

The invention disclosed by said Japanese Disclosure Gazette No. 1973-104381 can not achieve adequate sterilization for ahead of each sealed container since a temperature of medical fluid contained therein rises as said medical fluid absorbs microwave but a space confined within said heat does not absorb microwave and therefore no temperature rise occurs therein. Additionally, the temperature of said medical fluid which has once risen falls again upon contact with the container head. Thus, it is also impossible for this invention to achieve a satisfactory sterilization.

The invention disclosed by said Japanese Disclosure Gazette No. 1975-38985 requires a large-sized furnace as well as a considerably high microwave capacity and, depending on the kinds of medical fluid, it is difficult for this invention to obtain a sufficient temperature rise in the ampule. Moreover, the intensity of microwave is significantly uneven depending on locations within the furnace, so the individual ampules often present correspondingly different temperature rise ratios. In addition, adequate sterilization of the ampule head also can not be expected.

To compensate for such inadequate sterilizing effect of microwave, the prior art has employed the auto clave as auxiliary means. However, the auto clave makes it impossible to achieve a temperature control of the individual sealed containers and sometimes causes ingredients of medical fluid to be decomposed. Furthermore, the auto clave prevents the sterilizing treatment from being continuously done along a single process line.

To overcome such problems, the inventor of the present application has disclosed, in Japanese Patent Application Disclosure Gazette No. 1990-41162, a method for ampule sterilization utilizing microwave in which only a lower portion of each ampule is inserted through a slot formed through a top wall of an irradiator furnace connected to a square waveguide into the irradiator furnace so that a desired sterilization occurs doing movement of this ampule along the slot, said method being characterized by that a depth of the irradiator furnace or a distance between the ampule and a top surface of said slot is adjusted to control an irradiation amount for each ampule.

However, the invention disclosed in this Japanese Disclosure Gazette No. 1990-41162 relies only upon adjustment of the depth of the irradiator furnace or the distance between the ampule and the top surface of said slot inevitably resulting in a partiality of heating effect.

SUMMARY OF THE INVENTION

It is an object of the invention to eliminate said partially of heating effect within the irradiator furnace, to suppress the temperature difference not only within the individual sealed containers but also among the different sealed containers by controlling a heating efficiency depending on properties such as the electrical conductivity of a particular kind of medical fluid and the size of a particular sealed container and thereby to achieve a reliable sterilizing effect.

The object set forth just above is achieved, according to the present invention, by a method for sterilizing a sealed container utilizing microwave in which the sealed container is inserted through a slot formed through atop wall of an irradiator furnace connected to a square waveguide functioning to propagate the microwave into the irradiator furnace so that a desired sterilization occurs during movement of the sealed container along the slot, said method being characterized by that the sealed container is irradiated with microwave on a portion slightly lower than its middle level as the sealed container travels along a course in the proximity of an inlet of the irradiator furnace and then irradiated on a portion adjacent its bottom with microwave as the sealed container travels along a course in the proximity of an outlet of the irradiator furnace.

To realize such sterilizing method, the present invention provides an apparatus for sterilizing a sealed container utilizing microwave, including an irradiator furnace provided through its top wall with a slot and connected to a square waveguide functioning to propagate microwave and a conveyor bucket adapted to hold the respective sealed containers having their lower portions inserted through said slot into the irradiator furnace and to convey the respective sealed container along said slot, characterized by that the irradiator furnace is provided therein with a rail extending from the lowest level at the inlet of the irradiator furnace tot he highest level at the outlet of the irradiator furnace and serving to support the bottom of each sealed container.

With such method and apparatus of the present invention, the sealed container is lifted up on the way along the rail of the irradiator furnace and, in consequence, the sealed container begins to be heated on its portion slightly lower than its middle level in the proximity of the inlet, producing a convection current in medical fluid and then the sealed container is heated preponderantly on its bottom so as to minimize a temperature difference between top and bottom of medical fluid.

Since the container bottom is preponderantly irradiated with microwave in the proximity of the outlet, the immediately following sealed container also can be sufficiently irradiated with microwave, so the sealed containers are gradually heated and the temperature unevenness of the successive containers can be minimized.

Said sterilizing apparatus for sealed containers utilizing microwave may be additionally provided with a hot air furnace to heat-sterilize the heads of the respective sealed containers containing therein no medical fluid within the hot air furnace and thereby to assure that said container heads and the other portions containing therein no medical fluid are also reliable sterilized.

Said object is also achieved by said apparatus for sterilizing sealed container utilizing microwave wherein said rail is replaced by a narrow passage formed at the outlet of said irradiator furnace. With this arrangement, the ampule on which the direct irradiation with microwave has been completed is maintained thereby at a constant temperature and such heat thermostatic effect makes sterilization further reliable.

Said object is also achieved by said apparatus for sterilizing sealed container utilizing microwave wherein there is provided an IR (Infrared radiation) heater to thermostatically heat the sealed container conveyed out from the irradiator furnace so that medical fluid contained in said sealed container which has been heated up to a peak temperature at the outlet of the irradiator furnace is kept at this temperature during conveyance along the passage into an thermostatic station and this effect is further assured by the IR heater. In this manner, the interior of the sealed container is reliably sterilized.

Said object is also achieved by said apparatus for sterilizing sealed container utilizing microwave wherein, there is provided a conveyor belt adapted to conveyor the sealed containers to a screw which receives, in turn, the sealed containers and rotates to further convey said sealed containers received therein; wherein there is provided a sealed container feeding hopper including a feeding star wheel adapted to feed the sealed containers to a conveyor bucket; and wherein said sealed container feeding hopper further includes a sensor adapted to detect whether individual turns of screw groove are properly loaded with the sealed containers or not and auxiliary feeding guides adapted to, when said sensor detects that any of the individual turns of screw groove are not loaded with the sealed container, feed the sealed containers to such turns of screw groove. In this manner, the sealed containers are continuously fed from the sealed container feeding hopper to the sterilizer without any feed vacancy so the sealed containers successively fed are irradiated with a constant amount of microwave.

BRIEF DESCRIPTION OF THE DRAWINGS

The above and other objects of the invention will be seen by reference to the description taken in connection with the accompanying drawings, in which:

FIGS. 2A and 2B are plan and sectional views respectively, of a hopper 12 including a feed fail-safe mechanism;

FIGS. 3A, 3B and 3C illustrate the feed fail-safe mechanism, in which FIG. 3A is a detailed plan view thereof and FIG. 3B and 3C are plan view, respectively, showing operation of said feed fail-safe mechanism;

FIG. 4 is a sectional view taken along a line IV—IV in FIG. 1;

FIGS. 6A through 6C are sectional, side and front views, respectively, of a preheating station;

FIGS. 13A and 13B are sectional and front views, respectively, of the heating station;

DETAILED DESCRIPTION OF THE INVENTION

Figure 1:
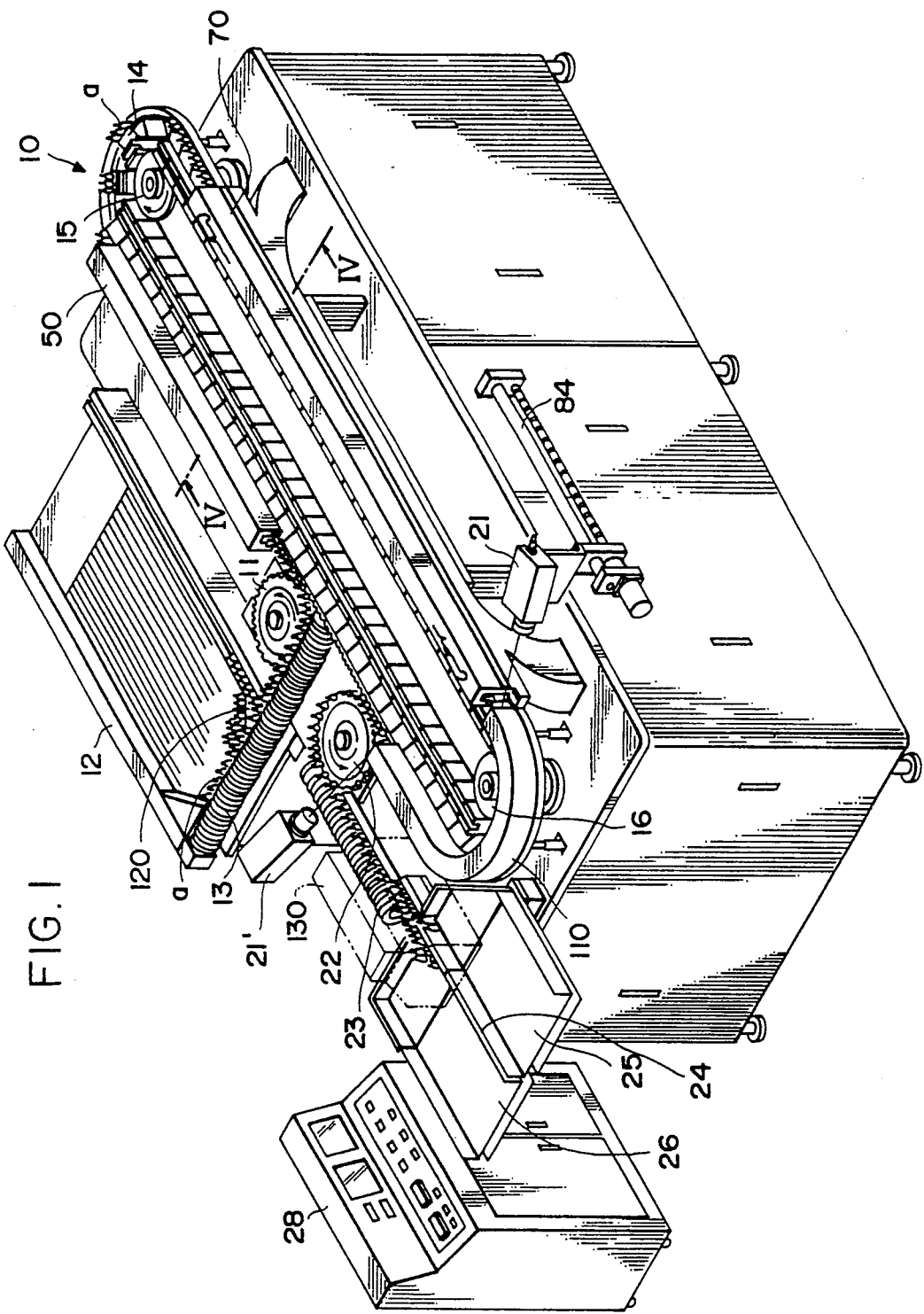
FIG. 1 is a perspective view of a sterilizer constructed according to the invention.

Although the invention will be described in reference with preferred embodiments taking an ampule as an example of the sealed container, it should be understood that the invention is not limited to the ampule and also applicable to the other containers filled with fluid such as bottle, vial and the like.

Outline of the invention will be explained with reference to a sterilizer 10 shown in FIG. 1. Reference numeral 11 designates a feed star wheel functioning to feed ampules (a) conveyed by a screw 13 from a hopper 12 into the sterilizer 10. Reference numeral 14 designates a conveyor bucket adapted to hold the ampules (a) and to convey them through the sterilizer. This conveyor bucket 14 is carried by an endless chain 17 running along a drive sprocket 15 and a follower sprocket 16 (see FIG. 4).

As this conveyor bucket 14 clockwise travels together with the respective ampules (a) held therein, the ampules (a) pass through a preheating station 50, a heating station 70 and a thermostatic station 110 and are subjected to sterilizing treatment during passage through these stations.

Reference numerals 21, 21' designate IR thermometers serving to take a temperature of each ampule (a) which has been heated and sterilized at the heating station 70 and the thermostatic station 110, respectively. As will be described later, said thermometer 21 is adapted also to be movable along a guide 84 to make follow-up temperature taking.

The ampules (a) thus sterilized are carried out by a discharge star wheel 22 and a screw 23, and then checked by the pair of IR thermometers 21, 21' respectively provided at two measuring locations whether the respective ampules are within a preset temperature range or not. Based on signals from these IR thermometers, a sorting guide 24 picks out the ampules (a) which are out of the preset temperature range as unacceptable products and thereby distributes the ampules (a) into an outlet for acceptable products 25 and an outlet for unacceptable products 26.

Reference numeral 130 designates a cooling unit used to cool the ampules (a), reference numeral 28 designates a control units for the sterilizer of the invention and it is in this control unit 28 that a temperature range for sterilization of the ampules is preset, output of microwave is automatically controlled so as to maintain a temperature rise of each ampules within a predetermined range in response to the signals coming from the IR thermometers 21, 21' and the sterilizer as a hole is controlled on the basis of judgment, for example, whether desired sterilization has been appropriately carried out or not.

Now the sterilizer of the invention will be described with respect to its respective parts. The ampules (a) filled with medical fluid are fed to the hopper 12. A feed fail-safe mechanism as shown by FIGS. 2A–3C assures that the ampules transported by the screw from the hopper are to the sterilizer 10 without any feed vacancy.

Figure 2A:
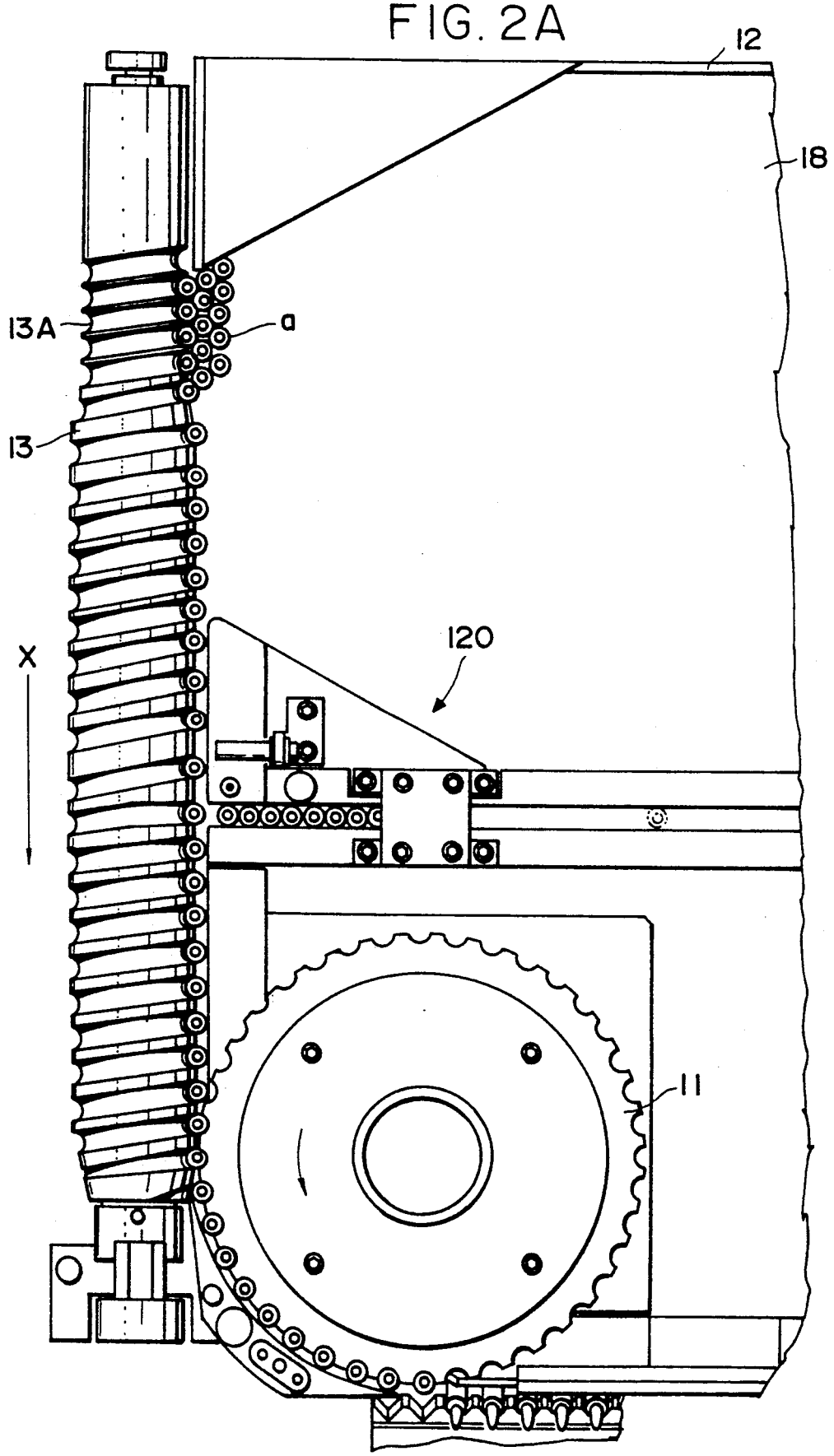

More specifically, there is provided on the termination of the hopper 12 the screw 13 to which the ampules (a) are continuously conveyed by a conveyor belt 18, as shown by FIGS. 2A and 2B.

The ampules (a) received in a spiral groove 13A of the screw 13 are transferred in a direction indicated by an arrow X in FIG. 2A, then fed at the termination of the screw 13 to the feed star wheel 11, and finally fed by the conveyor bucket 14 into the sterilizer 10 of the invention.

Said hopper 12 is provided with a feed fail-safe mechanism 120 assuring that the ampules (a) are continuously fed to the sterilizer without any feed vacancy.

Specifically, the feed fail-safe mechanism 120 includes, as seen in FIG. 3A, a pair of auxiliary feeding guides 122, 123 between which the ampules (a) are normally biased by the conveyor belt 18 toward the screw 13.

Reference numeral 124 designates a photosensor to detect that any ampule (a) have not been properly received in the spiral groove 13A of the screw 13 and a toothless appearance has occurred, reference numeral 125 designates a pair of air jet nozzles provided adjacent the termination of the auxiliary feeding guides 122, 123 at two vertically opposite locations on the inner surface, and reference numeral 126 designates a valve.

So long as the screw 13 continuously feed the ampules (a) without any feed vacancy, the valve 126 remains opened allowing the air jet nozzles 125 to provide air blast which prevents the ampule (a) existing between the auxiliary feeding guides 122, 123 from being in contact with the ampule (a) received in the spiral groove 13A.

Figure 3B:
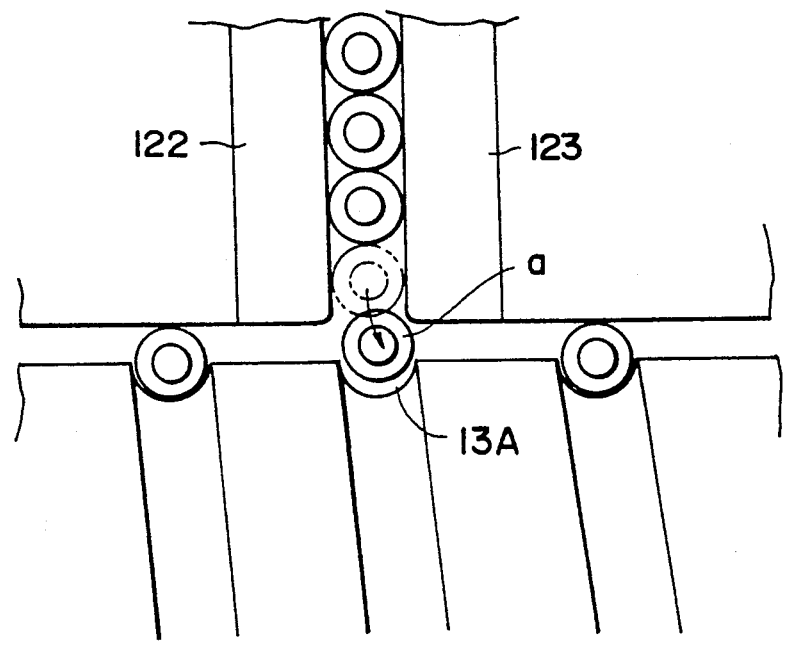

When the photosensor 124 denotes a toothless, i.e., ampule-free turn along the spiral groove 13A of the screw 13, the valve 126 is closed, stopping supply of the air blast from the air jet nozzles 125 and, as seen in FIG. 3B, the ampule (a) stored between the auxiliary feeding guides 122, 123 is fed top said ampule-free turn of the spiral groove 13A. Thus, the ampules (a) are continuously fed to the sterilizer without feed vacancy.

Figure 3C:
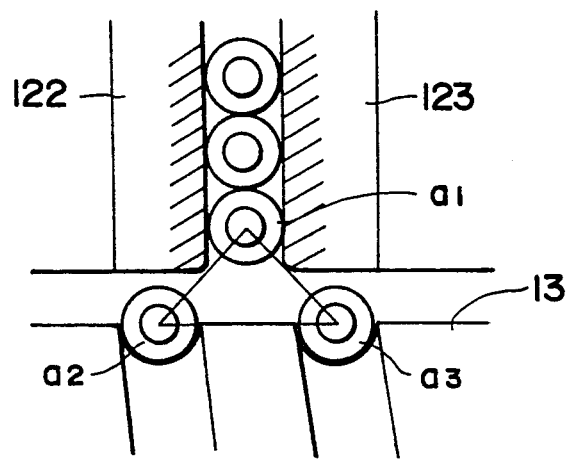

Referring to FIG. 3C, the feed fail-safe mechanism 120 may be positioned relative to the ampule (a1) stored between the auxiliary feeding guides 122, 123 and to the ampules (a2), (a3) transported by the screw 13 so that an equilateral triangle is defined by said feed fail-safe mechanism 120 and the ampules (a1), (a2), (a3). In this way, smooth feeding of the ampules (a) is assured.

Thus, the ampules (a) are continuously fed to the conveyor bucket 14 of the sterilizer 10 without a feed vacancy.

Now a mechanism causing the ampules (a) to travel through the sterilizer 10 will be discussed in reference with FIGS. 1, 4, 5A and 5B.

The endless chain 17 running along the sprockets 15, 16 is provided with a plurality of bearing cases 30 being closely adjacent one to another, each of which is provided with a plate 31 which is, in turn, provided with each of the conveyor bucket 14.

As will be apparent from FIG. 4, each bearing case 30 contains therein an upper bearing 32 and a lower bearing 33 through which a pair of horizontal guide rods 34, 35 stationary mounted on the sterilizer 10 so that the bearing cases 30, the plates 31 and the conveyor bucket 14 can maintain their predetermined postures during traveling through the sterilizer.

Figure 5A:
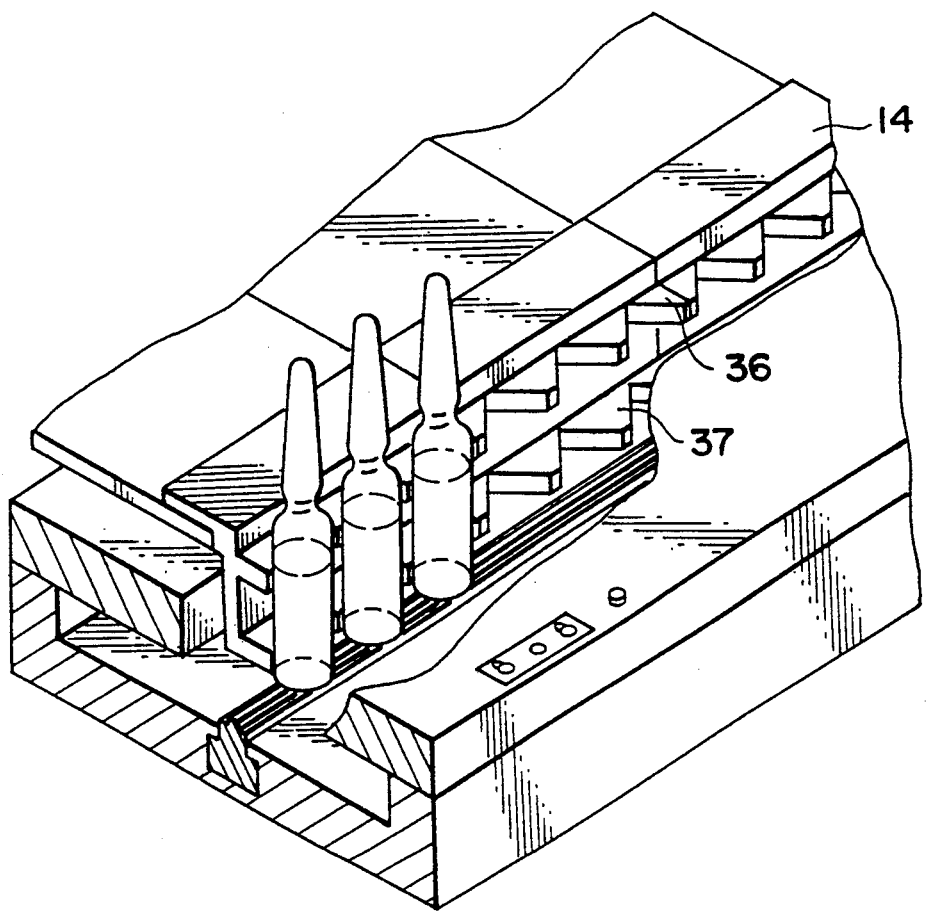
FIGS. 5A and 5B are plan and sectional views respectively, showing a conveyor bucket as holding ampules.

Referring to FIG. 5A, the conveyor bucket 14 includes a series of upper triangular projections 36 and a series of lower triangular projections 37 which are parallel to each other and define spaces 38 therebetween.

As seen in FIG. 4, the conveyor bucket 14 is slightly tilted inside to the vertical and the ampules (a) are held in a tilted posture between the projection 36, 37 during clockwise traveling together with the conveyor bucket 14.

Reference numeral 44 designates a rail adapted to support the bottom of each ampule (a) as the ampule (a) travels through the preheating station 50, reference numeral 46 designates a sorting guide to prevent the ampule (a) from slipping out of the conveyor bucket 14 and reference numeral 40 designates a rail provided within the irradiator furnace of the heating station 70 (see FIG. 4).

The ampules (a) are carried by the conveyor bucket 14 in the manner as has been described above and successively pass through the preheating station 50, the heating station 70 and the thermostatic station 110, as will be described in detail later. Thus, the ampules are subjected to the sterilizing treatment.

The preheating station 50 will be discussed in reference with FIGS. 1 and 6A–C.

Referring to FIG. 1, the ampules (a) fed by the feeding star wheel 11 to the sterilizer 10 are introduced into the preheating station 50.

Figure 6A:
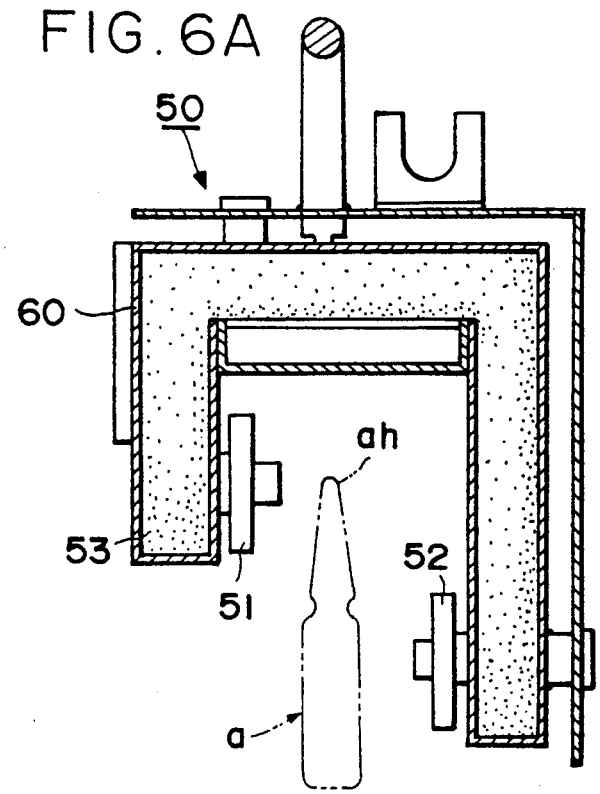
Figure 6B:
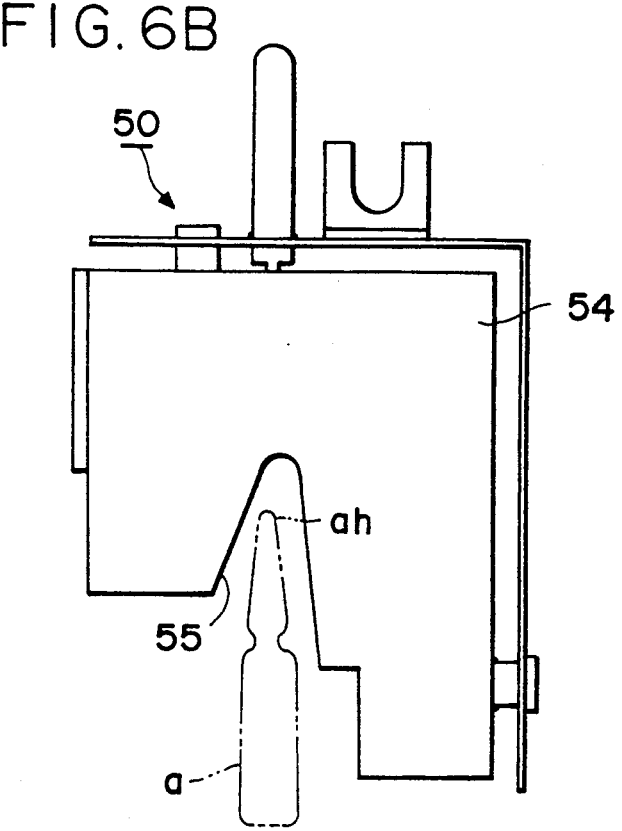

As shown by FIG. 6A, the preheating station 50 comprises a preheating case 60 having a gate-shaped cross-section and within the preheating case 60 there are provided a pair of IR heater 51, 52 on both sides of the ampule (a), respectively. Reference numeral 53 designates a heat insulating wall. Referring to FIG. 6B, both inlet and outlet sides of the preheating case 60 are also provided with a heat shielding wall 54 to protect the case 60 against heat leakage. Reference numeral 55 designates a notch allowing the heat (ah) of the ampule (a) to pass through the heat shielding wall 54.

In the preheating station 50, the one IR heater 51 provided as the upper heater adapted to preheat preponderantly the head (ah) of each ampule (a) which is filled with no medical fluid while the heater 52 is located at a level slightly lower than said heater 51 so that an inner mediate portion of each ampule (a) is preheated. It should be understood that a preheating temperature of these heaters 51, 52 is sensed, for example, by a thermocouple or the like and controlled by the control unit 28 at a preset temperature.

With the thermic rays radiation heaters or the like which have been conventionally used, a heating efficiency would be inadequate and will produce uneven temperature risen for respective ampules (a) because such thermic rays have their wavelength substantially equal to those of visible rays and tend to be reflected by the surface of each ampule (a). On the contrary, the invention uses the IR heaters which are capable of producing heat having a wavelength of 4 to 8 microns and the least reflectiveness on the ampule surface made of borosilicate soda glass, and thereby increases the heat absorptive efficiency form the conventional level of 50% up to 80%. Thus, unevenness in the temperature for respective ampules (a) can be also minimized. Typically, these heaters 51, 52 heat the ampules (a) up to about 50° C. to 60° C.

As shown by FIG. 6C, the preheating case 60 of the preheating station 50 is supported by a pair of supports 56, 56 which are vertically movable within a pair of guide cylinders 57, 57, respectively, so that a cylinder unit 61 carried by a cross member 58 extending between said pair of supports 56, 56 may be activated to move the preheating case 60 as a whole in a vertical direction.

The ampules (a) fed to the sterilizer 10 in the manner as has been mentioned above travel together with the conveyor bucket 14 holding said ampules therein and have their heads and intermediate portions preheated by this preheating station 50.

preheating of the ampule (a) in the preheating station economically saves the amount of microwave irradiation performed in the heating station as will be described later.

Even if the ampules (a) present more or less temperature difference depending on conditions, for example, how these ampules (a) have been stored, these ampules (a) will be heated up to a substantially constant temperature as the pass through the preheating station 50.

Now the heating station 70 will be explained in reference with FIGS. 7 through 13E.

The ampules (a) having passed through the preheating station 50 in the sterilizer 10 is then introduced into the heating station 70.

Figure 7:
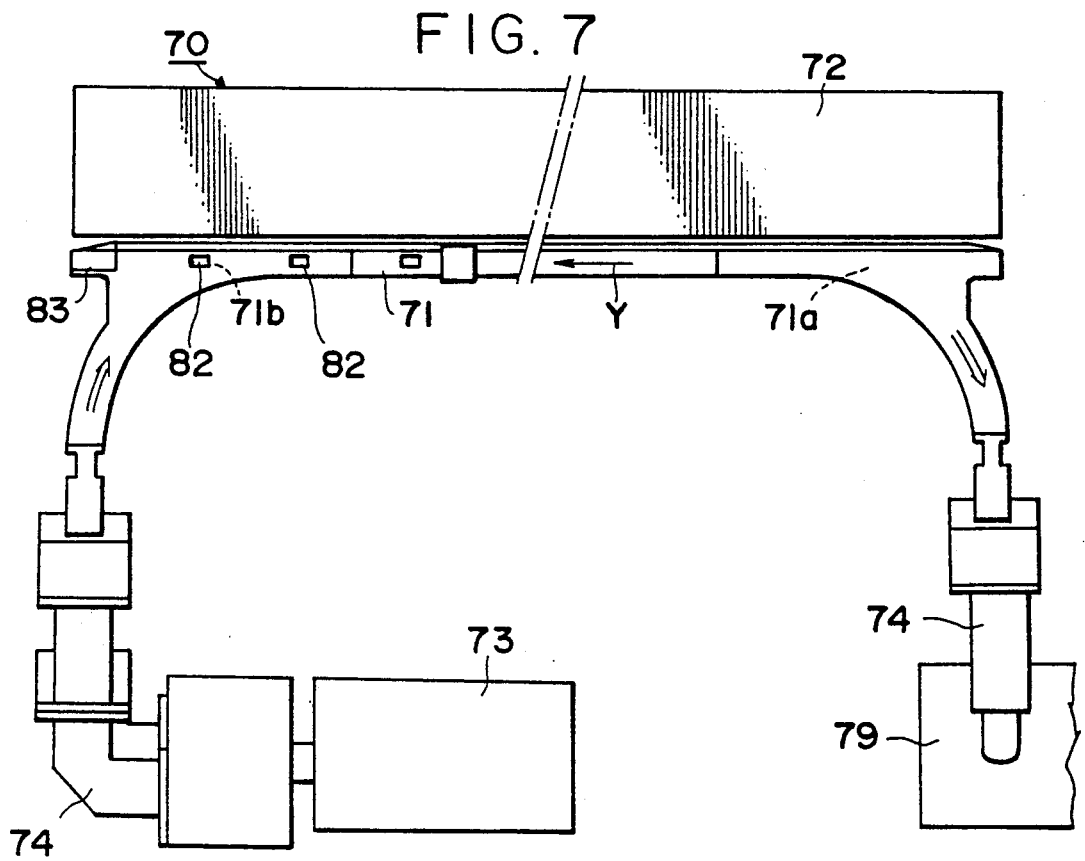
FIGS. 7 and 8A are front and plan view, respectively, showing a heating station.

Referring to FIG. 7, the heating station 70 comprises a hot air case 72 extending above the ampules (a) and an irradiator furnace 71 adapted to irradiated a lower portion (aL) of each ampule (a).

First, the irradiator furnace 71 will be discussed in reference with FIGS. 7 through 9C.

Referring again to FIG. 7, reference numeral 73 designates a microwave oscillator, reference numeral 74 designates a square waveguide functioning to propagate microwave and reference numeral 79 designates an absorber for excessive microwave. A horizontal portion of the square waveguide 74 forms the irradiator furnace 71.

Figure 8A:
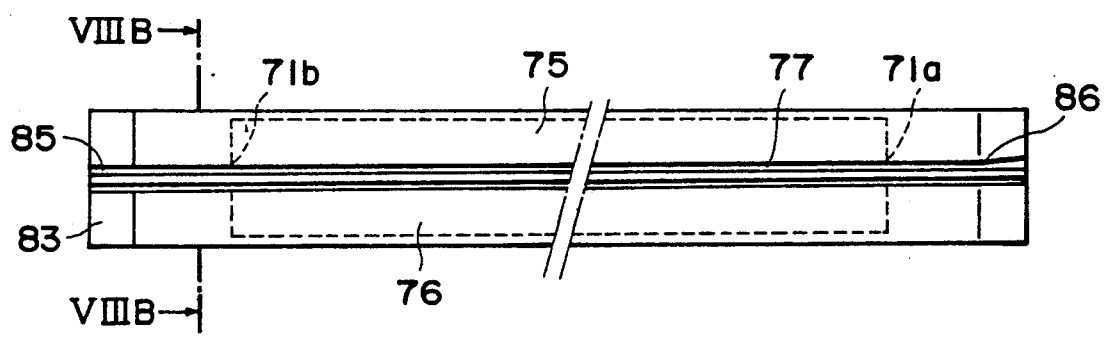
Figure 8B:
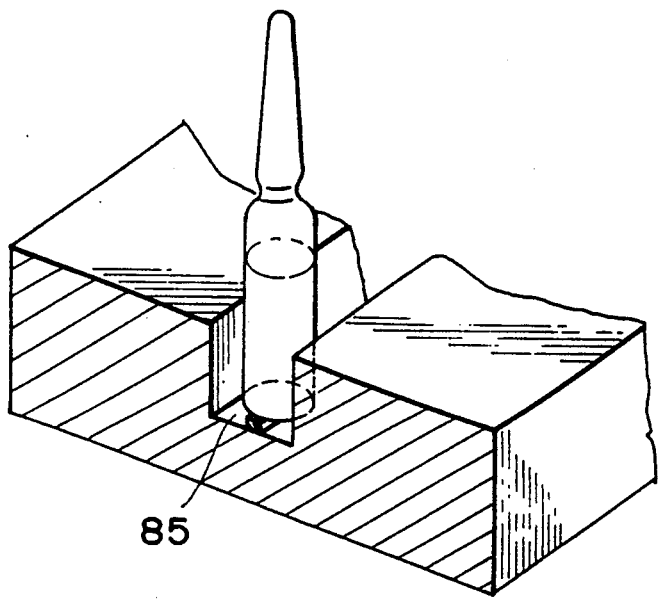
FIG. 8B is a sectional view taken along a line B-VIII B of FIG. 8A.

As seen in FIG. 8A, a top wall of the irradiator furnace 71 comprises a pair of top plates 75, 76 between which a slot 77 is formed.

Referring back to FIG. 4, the ampules (a) which have been conveyed by the conveyor bucket 14 to the heating station 70 travel through the heating station 70 with only their lower portions (aL) inserted through said slot 77 into the irradiator furnace 71. It should be noted here that the ampule (a) travel from an inlet 71a towards an outlet 71b of the irradiator furnace 71 in a direction indicated by an arrow Y, i.e., in the reverse direction with respect to the microwave irradiation (see FIG. 7).

Figure 9A:
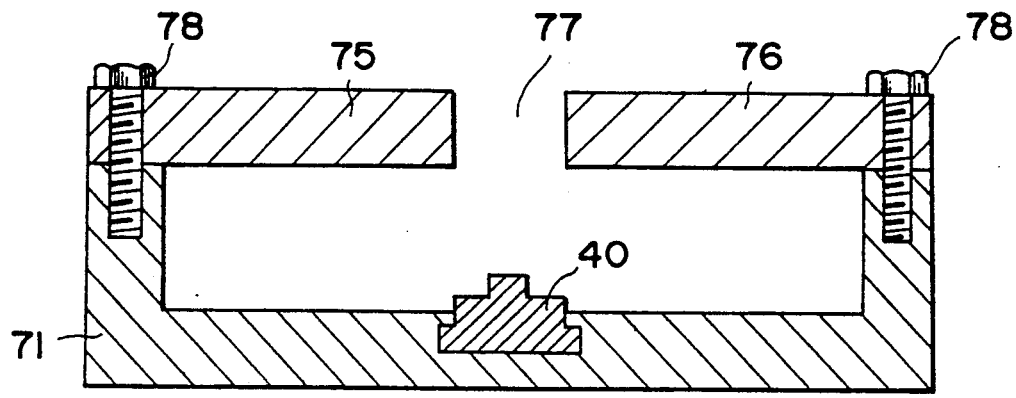
FIGS. 9A through 9C are sectional views, respectively, showing variants of the irradiator furnace.
Figure 9B:
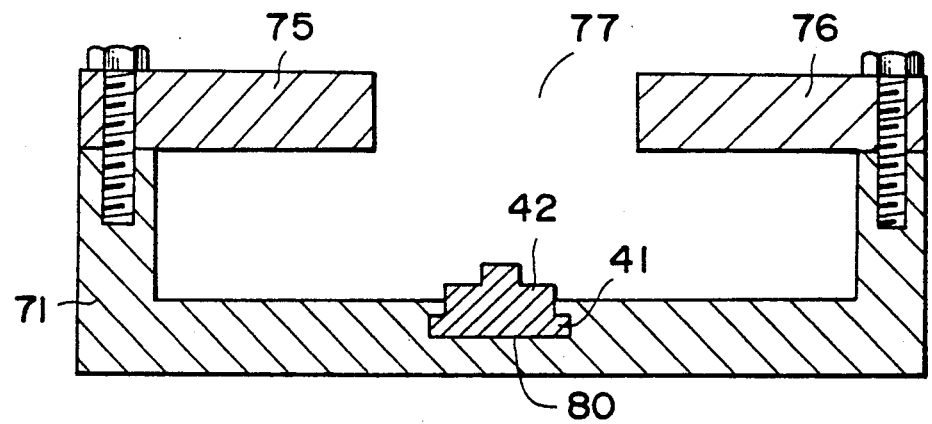
Figure 9C:
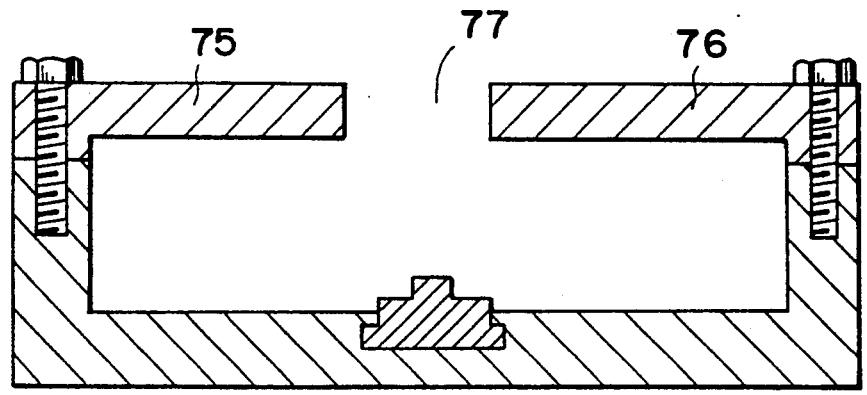

The top plates 75, 76 of the irradiator furnace 71 are replaceable and, as shown by FIGS. 9A through 9C, both or any one of these top plates 75, 76 may be replaced by those or that of desired size(s) and configuration(s) to adjust a width of the slot 77 and or a depth of the irradiator furnace 71. Reference numerals 78 designate screws for fixation of the top plates.

A rail 40 mounted on a floor of the irradiator furnace 71 is also replaceable and may be replaced by that of a desired height to adjust a depth of the ampule's lower portion (aL). Teflon is suitable as material of this rail 40.

The rail 40 presents a stepped cross-section and first steps 41 are engaged in associated cavity-like grooves 80 formed in the floor of the irradiator furnace 71 to present the rail 40 from being lifted out (see FIG. 9B).

Figure 10:
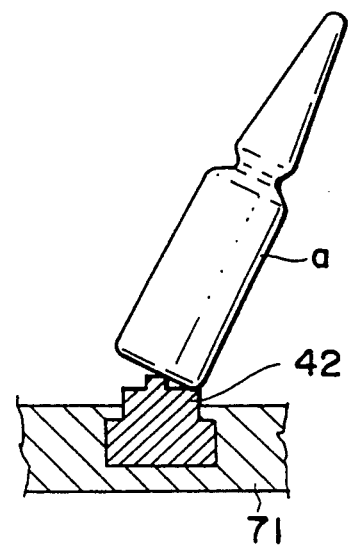
FIG. 10 illustrates the ampule tilting with respect to a bottom of the irradiator furnace.

Second steps 42 of the rail 40 project above the floor of the irradiator furnace 71 so that, even if the ampule (a) tilts as shown by FIG. 10, any one of these second steps 42 will come into contact with the bottom of the ampule (a) and thereby prevents the bottom of the ampule(a) from coming into direct contact with the floor of the irradiator furnace 71. In this way, undesirable spark can be effectively avoided.

Figure 11:
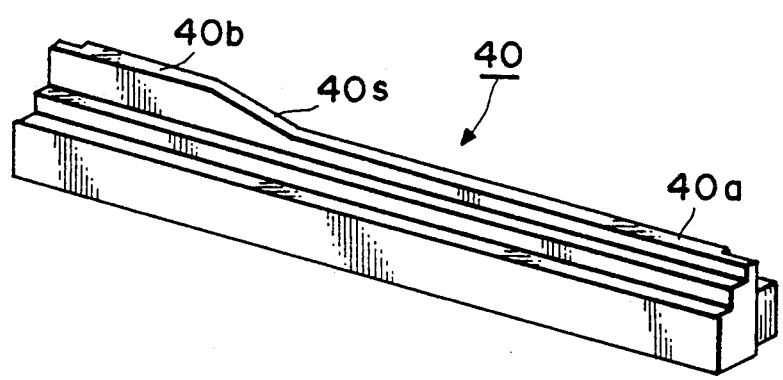
FIG. 11 is a perspective view of a rail.

As seen in FIG. 11, the rail 40 includes a slope portion 40s, and is low along a length 40a extending from said slope portion 40s to the inlet of the irradiator furnace 71 and high along a length 40b extending from said slope portion 40s to the outlet of the irradiator furnace 71.

Figure 5B:
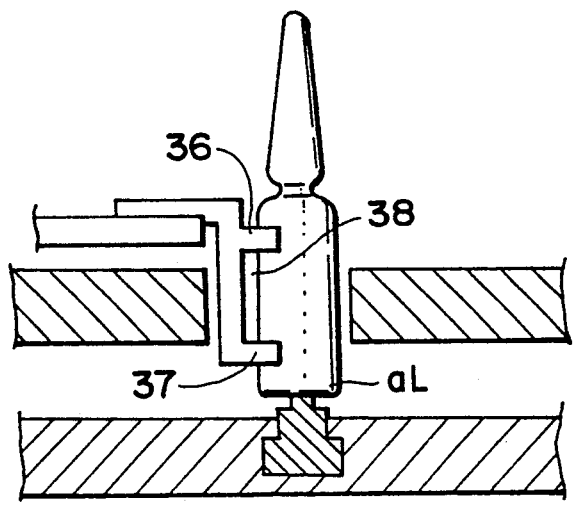

FIG. 5A, 5B illustrate how the ampules (a) are held by the triangular projections 36, 37 of the conveyor bucket 14 with their portions (aL) inserted into the irradiator furnace 71. Said lower portions (aL) are irradiated with microwave and medical fluid contained in the respective ampules (a) is heated by absorbing the microwave energy as the ampules (a) travel along the slot 77. As has been mentioned in connection with FIG. 7, the direction of microwave irradiation is reverse to the traveling direction of the ampules (a), the intensity of microwave irradiating the ampules (a) increase as the ampules (a) approach the outlet of the irradiator furnace 71.

Figure 12:
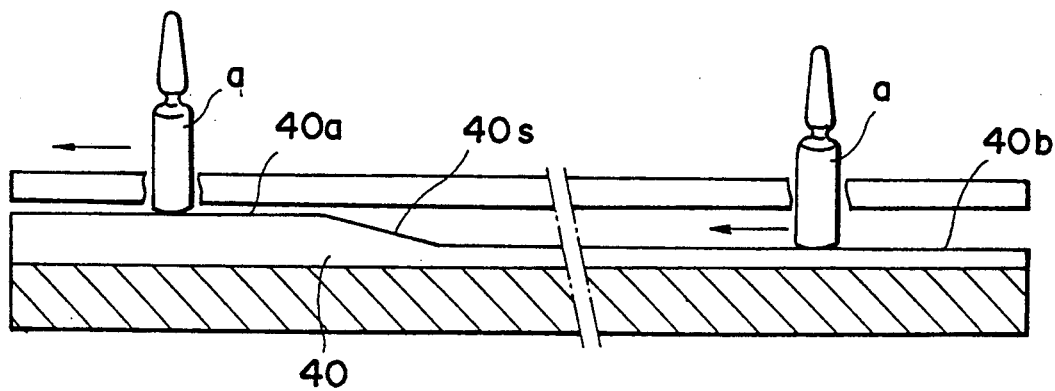
FIG. 12 is a sectional view of the irradiator furnace taken along a plane perpendicular to the plane of FIG. 9.

The ampules (a) is lifted up as they travel along the slope portion 40s of the rail 40 because the bottom of each ampule (a) slidable on the rail 40 (see FIG. 12).

As seen in FIG. 7, the irradiator furnace 71 is provided in a side wall with a plurality of windows 82 and at the outlet end with a notch 83 formed by partially cutting the side wall away. The IR thermometer 21 as shown in FIG. 1 travels along a guide 84 for this thermometer 21 in parallel with the irradiator furnace 71 at the same velocity as the ampule (a) so that said thermometer 21 can measure a temperature of the ampule (a) traveling within the irradiator furnace 71 through said windows 82 and said notch 83 so as to determine a variation in the temperature rise of said ampules (a).

It should be understood that, if it is unnecessary to known such variation in the temperature rise of said ampule(a), the IR thermometer 21 may be fixed to the outlet end of the irradiator furnace 71.

The temperature of medical fluid contained in the ampule (a) may be taken at a location where medical fluid normally prevents the highest temperature, for example, a location adjacent the fluid surface and at a location where medical fluid normally presents the lowest temperature, for example, a location adjacent the ampule bottom in order to determine a temperature difference developed in medical fluid. However, if dependable measurement data are available, the temperature may be taken at a single location.

The irradiator furnace 71 as has been mentioned above has a rectangular configuration as viewed in the plan view of FIG. 8A and provided adjacent the outlet 71b and the inlet 71a with passages 85, 86, respectively, which are of the same width as the slot 77 (see FIG. 8B) so that the ampule (a) coming out from the irradiator furnace 71 onto the passage 85 absorbs an energy of microwave leaking through the outlet 71b of the irradiator furnace 71 and thereby the temperature of the ampule (a) which has been heated within the irradiator furnace 71 is effectively kept along the passage 85. In this manner, after having been heated a within the irradiation furnace 71, the ampules (a) is kept warm along the passage 85 and then transferred to the thermostatic station 110.

The width of said passage 85 is same as the slot 77 and depends on the size of the ampule (a). For example, the width of the passage 85 will be in the order of 25 mm for the ampule (a) having a diameter of 10 mm. To accommodate an ampule of different size, the passage width may be correspondingly changed by appropriately replacing members or components.

Then, the hot air case 72 provided above the irradiator furnace 71 will be discussed.

Figure 13A:
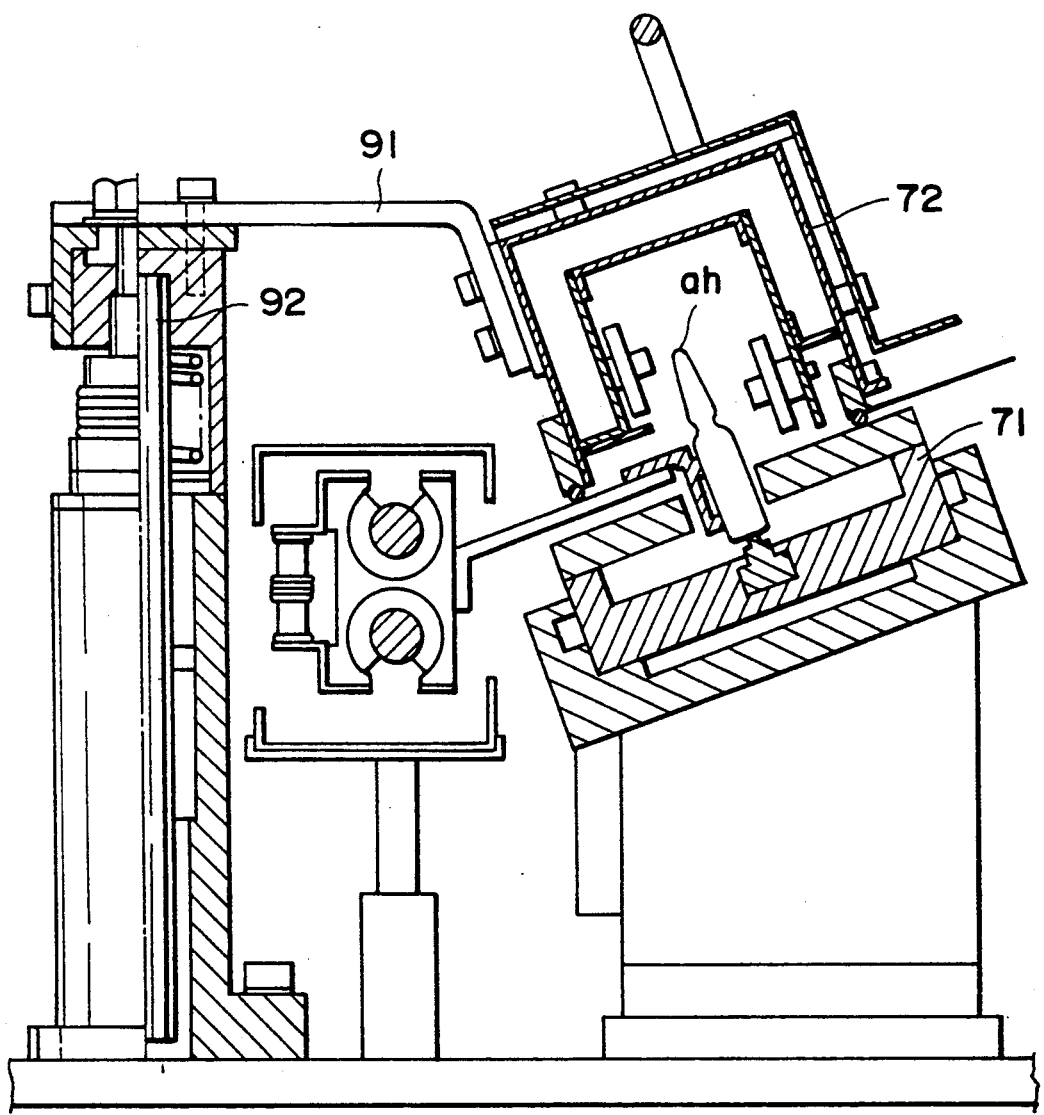
Figure 13C:
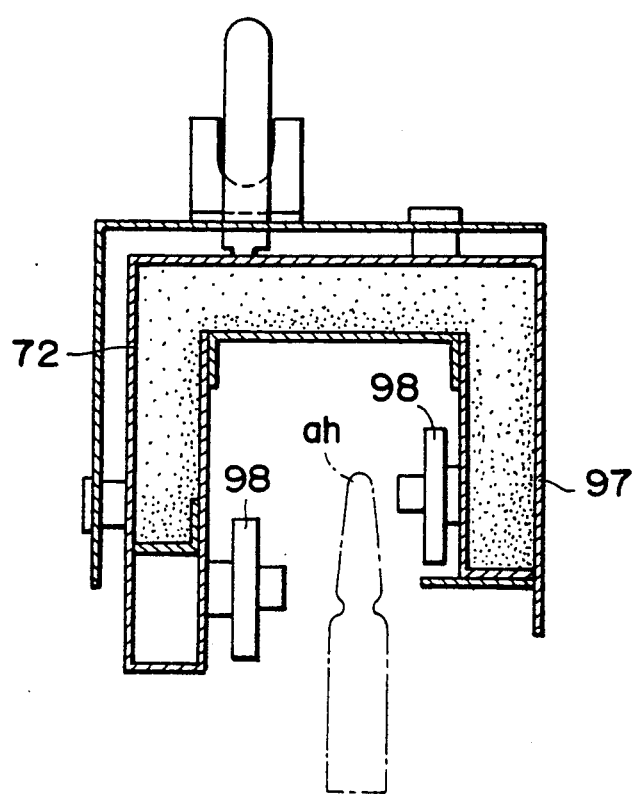
FIG. 13C is a sectional view of a hot air furnace taken along a line X III C- X III C in FIG. 13B.

Similarly to the already explained preheating station 50, the hot air case 72 presents a gate-shaped cross-section a shown by FIG. 13A, and is supported by an arm 91 and supports 92 so as to cover the heats (aH) of the respective ampules (a) projecting out through the slot 77 of the irradiator furnace 71.

Referring to FIG. 13B air heaters 93a, 93b are mounted on the top of the hot air case 72, and air ducts 94a, 94b are connected to these air heaters 93a, 93b, respectively, and provided from nozzles 95 of the hot air case 72 in the form of hot air blast. Reference numeral 96 designates a cover surrounding the heads (ah) of the ampules (a) and adapted to direct the hot air blast so that the hot air blast reliably strikes against the ampule heads (ah).

In the illustrated embodiment of the hot air case 72, the air heater 93a on the inlet side provides air blast heated approximately at a temperature of 140° C. and thereby rapidly heats the heads (ah) of the ampules (a) successively introduced into the heating station 70 while the air heater 93b on the outlet side provides air blast heated approximately at a temperature of 170° C. to 180° C. and thereby heats the heads (ah) of the ampules (a) to a predetermined temperature for sterilization.

Reference numeral 97 designates a heat insulating wall to keep the interior of the hot air case 72 warm and reference numerals 98, 98 designate IR heaters provided within the hot air case 70 on opposite sides, respectively. It should be understood that these IR heaters 98, 98 heat the interior of the hot air case 72 at a temperature in the order of 50° C. to 60° C. to keep the interior of the hot air case 72 warm but these IR heaters are not always necessary.

Figure 13D:
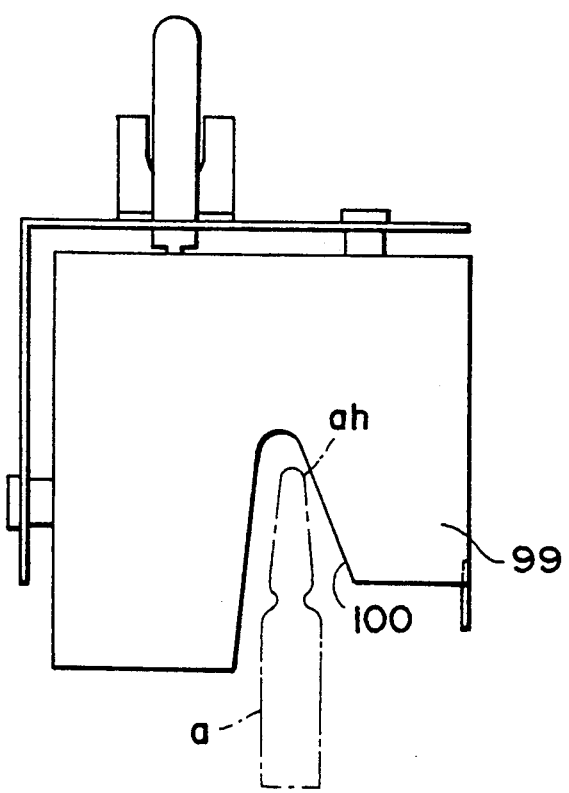
FIG. 13D is a side view of the hot air furnace.
Figure 13E:
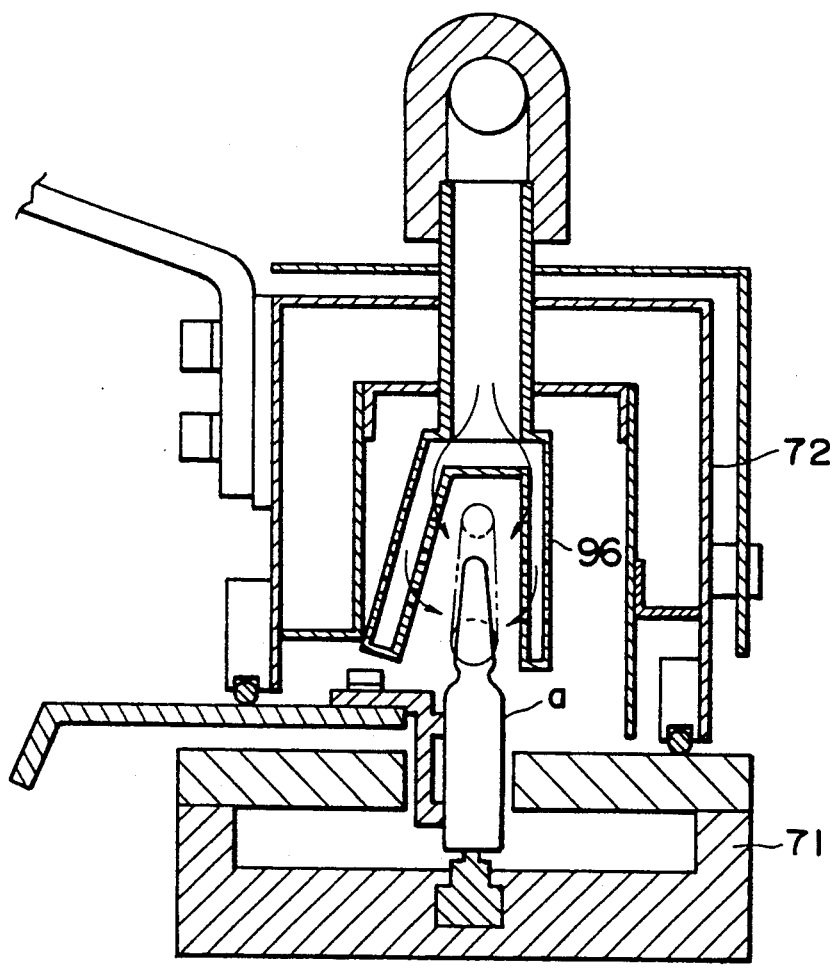
FIG. 13E is a sectional view taken along a line X III E- X III E in FIG. 13B.

Similarly to the preheating case 60, the hot air case 72 includes a heat shielding wall 99 at the inlet and the outlet for the ampules (a) on both sides, as seen in FIG. 13D, in order to shield a heat leakage. Reference numeral 100 designates a notch allowing the heads (ah) of the ampules (a) to pass through the heat shielding wall 99 without hindrance.

Referring to FIG. 13B, reference numerals 101, 102 designate guide cylinders adapted to carry the supports 92 in a vertically movable manner. A cylinder unit 104 mounted on a cross member 103 extending between the supports 92, 92 may be activated to move the entire hot air case 72 in a vertical direction.

The manner in which the ampules (a) are heated by the heating station may be summarized as follows:

Specifically, the ampules (a) coming out from the preheating station 50 travel along the slot 77 of the irradiator furnace 71 together with the conveyor bucket 14 holding these ampules (a)therein, passing thus through the heating station 70, and, during the passage through the heating station 70, the irradiator furnace 71 irradiates the ampule lower portions (aL) with microwave so that medical fluid contained in the respective ampules (a) absorbs such a microwave energy and is sufficiently heated to be sterilized. Since the microwave is irradiated in a direction reverse to the direction in which the ampules (a) travel, an intensity of microwave with which the respective ampules (a) are irradiated increases as the respective ampules (a) go ahead within the irradiator furnace 71 and it is assured that the ampules (a) are gradually heated up to a peak temperature attained by them at the outlet 71b of the irradiator furnace 71.

Since the respective ampules (a) are successively lifted up as they travel along the slope portion 40s of the rail 40 extending in the irradiator furnace 71, the ampules (a) which have been irradiated on their portions slightly lower than the middle level along the first half 40a of the rail 40 are now irradiated primarily on their lower portions with microwave as they move from the sloe portion 40a to the second half 40b of the rail 40, thus a portion of medical fluid occupying the lower portion of each ampule (a) is preponderantly heated and sterilized.

An area on each ampule (a) exposed to microwave irradiation decreases as this ampule (a) is lifted up along the slope portion 40a of the rail 40 and an amount of microwave energy being absorbed by this ampule (a) also decreases. A s a result, the following ampules (a) can be irradiated with sufficient microwave to assure that the respective ampules (a) are gradually heated along their traveling course from the inlet 71a to the outlet 71b of the irradiator furnace 71.

In this manner, the ampules (a) are heated first on their portions slightly lower than the middle level, as previously mentioned, so as to heat the portion of medical fluid occupying the portion of each ampule (a) above said middle level and then heated so that the entire quantity of medical fluid contained in each ample (a) can be uniformly heated.

As has already been described. The feed fail-safe mechanism 120 incorporated in the hopper 12 assures that the sterilizer 10 is continuously supplied with the ampules (a) without a feed vacancy and thereby the amount of microwave irradiation to the respective ampules (a) is maintained at a constant level. More specifically, if there occurs a toothless location along the conveyor bucket running through the irradiator furnace 71, approximately five to seven ampules (a) existing before and after said toothless location would be excessively heated at a temperature higher than the preselected temperature for sterilization by 20° C. to 30° C. and these ampules (a) would be come unacceptable products. However, such a problem is avoided in accordance with the invention by providing the hopper 12 with said feed fail-safe mechanism 120.

While medical fluid contained in each ampule (a) is heated and sterilized by the irradiator furnace 71, the heat (ah) of this ampule (a) is also heated and sterilized within the hot air case 72.

The ampule (a) thus heated up to the peak temperature at the outlet 71b of the irradiator furnace 71 travels through the passage 85 without loss of this peak temperature because, along this passage, the ampule (a) continues to absorb the microwave energy leaking through the outlet 71b of the irradiator furnace 71.

Now the thermostatic station 110 will be discussed in reference with FIGS. 14A-D.

Referring again to FIG. 1, the ampules (a) having passed through the preheating station 50 and then the heating station 70 are introduced into the thermostatic station 110.

Figure 14A:
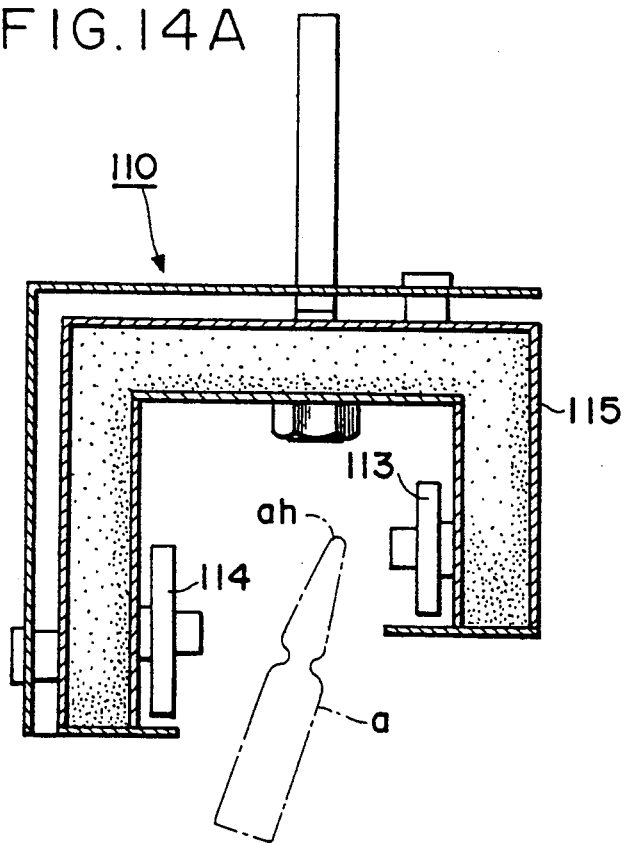
FIGS. 14A through 14D are sectional, side, plan, and front views, respectively, of a thermostatic station.

Similarly to the above-mentioned preheating station 50 and hot air case 72, the thermostatic station 110 comprises thermostatic case 119 presenting a gate-shaped cross-section, as shown in FIG 14A.

Figure 14B:
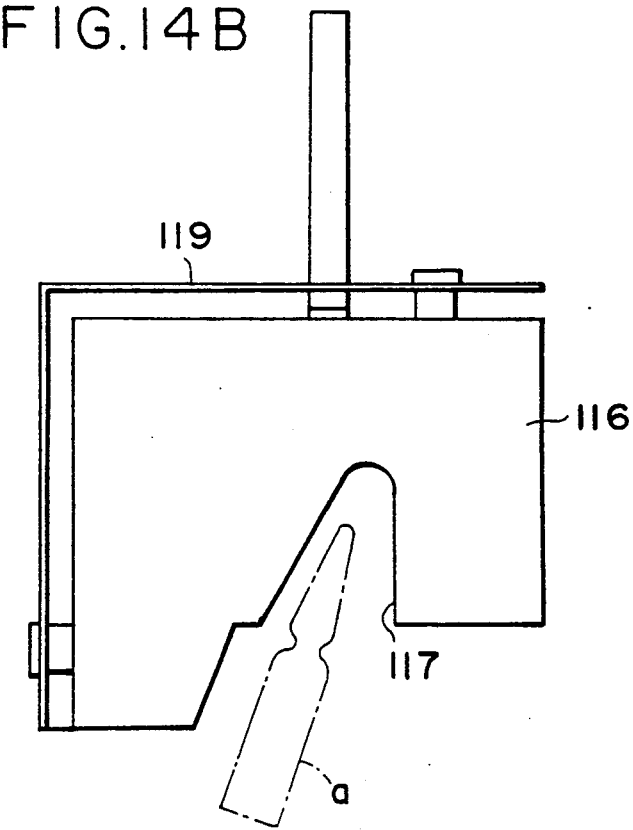
Figure 14C:
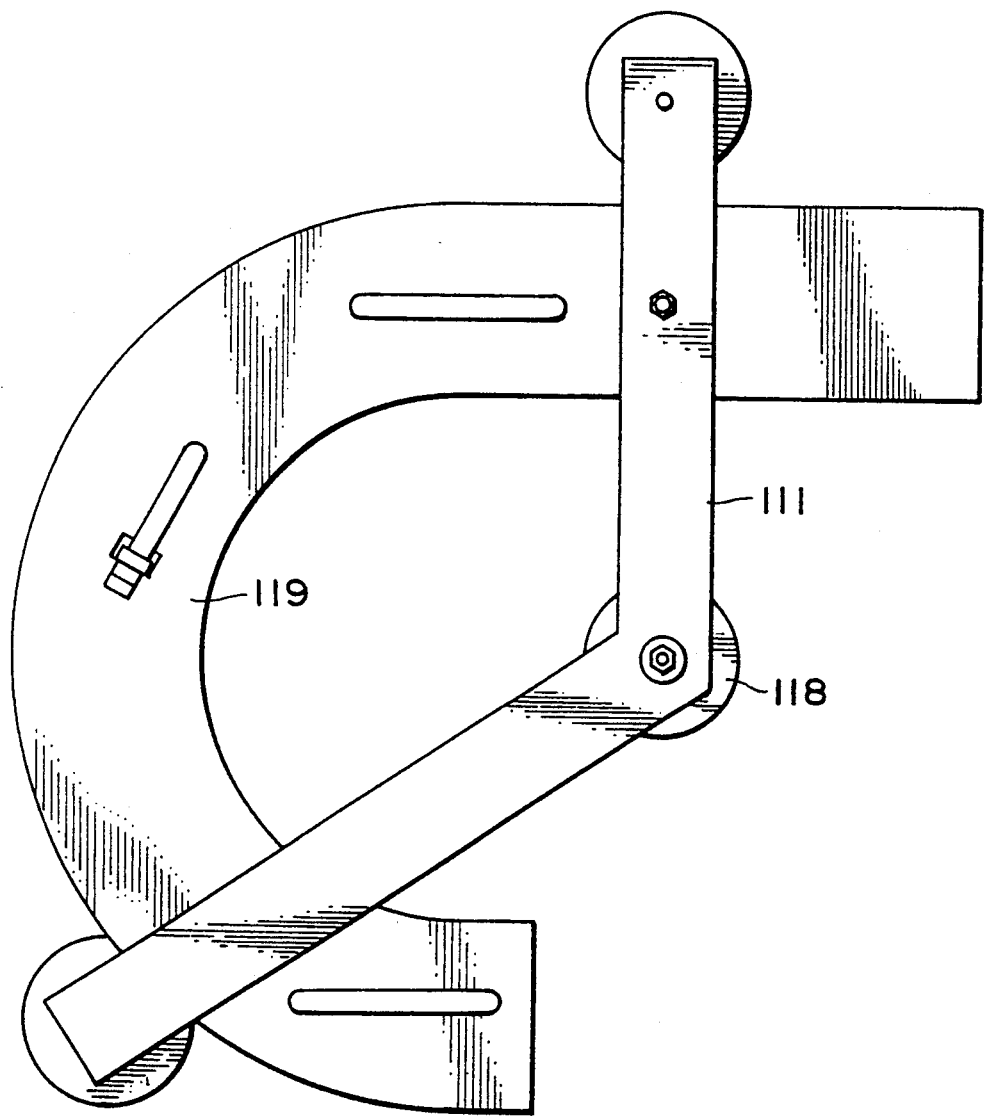
Figure 14D:
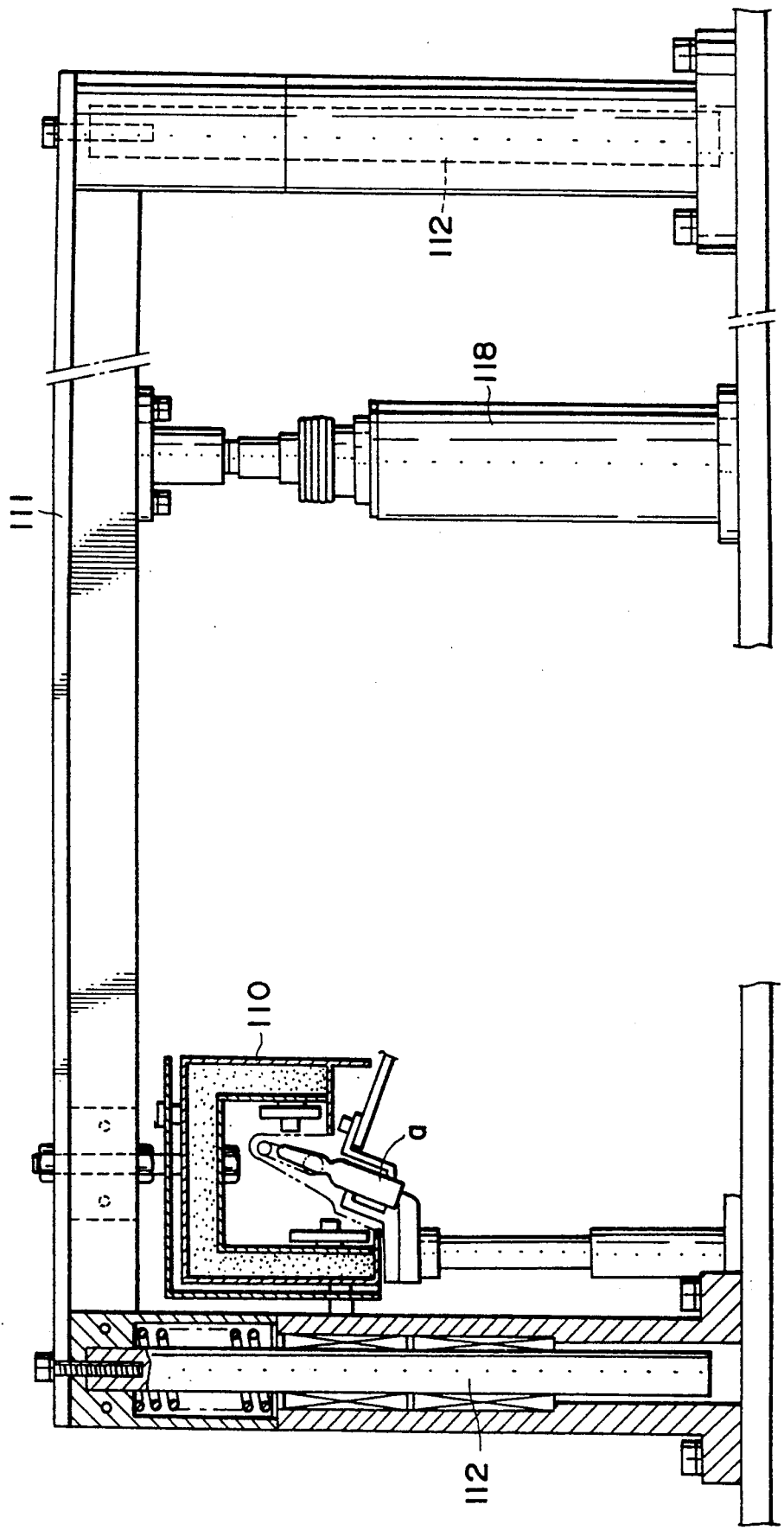

Referring to FIG. 14D, the thermostatic case 119 is supported by an arm 111 and supports 112 so as to extend above the ampules (a) and contains therein a pair of IR heaters 113, 114 positioned on both sides of the ampules (a), respectively. Reference numeral 115 designates a heat insulating wall. The heater 113 positioned at a relatively high level serves to heat primarily the head (ah) of each ampule (a) while the heater 114 positioned at a relatively low level serves to heat primarily the intermediate portion of each ampule (a). Use of the IR heater, as in accordance with the invention, generally facilitates a temperature control and is more effective than the hot air heater to maintain entire medical fluid at a uniform temperature. Furthermore, the IR heater is advantageous also in that the thermostatic case 119 is free from a heat leakage, a god working environment is provided and manufacturing cost is reduced.

Similarly to the preheating case 60 and the hot air case 72, the thermostatic case 119 is provided with front and rear sides with heat shielding walls 116 for prevention of heat leakage. Reference numeral 117 designates a notch formed in the heat shielding wall 116, as seen in FIG. 14B, so that the ampule head (ah) can freely pass by these heat shielding walls 116.

Referring to FIG. 14D, the thermostatic case 119 is moved upward as a cylinder unit 118 is actuated.

Thus, the ampules (a) heated in the heating station 70 up to the peak temperature pass through the thermostatic station 110 together with the conveyor bucket holding these ampules (a) therein and, in the thermostatic station, they are maintained at said peak temperature.

In this manner, the ampules (a) are heated in the heating station 70, then maintained at this condition in the thermostatic station 110 and thereby the sterilizing effect is significantly enhanced.

The ampules (a) thus subjected to the sterilizing treatment by passing through the preheating station 50, the heating station 70 and the thermostatic station 110 are then taken by the discharging star wheel 22 out from the conveyor bucket 14 and transported by the screw to the sorting guide 24 (see FIG. 1).

Depending on the signal applied from the control unit 28, the sorting guide 24 guides only the ampule (a) which has been determined by the IR thermometer 21, 21' provided on two temperature taking locations to be at a predetermined temperature range for sterilization onto the outlet 25 exclusively for acceptable products and, for the other ampules (a), said sorting guide 24 clockwise rotates to guide such ampules (a) onto the outlet 26 exclusively for unacceptable products.

Figure 15:
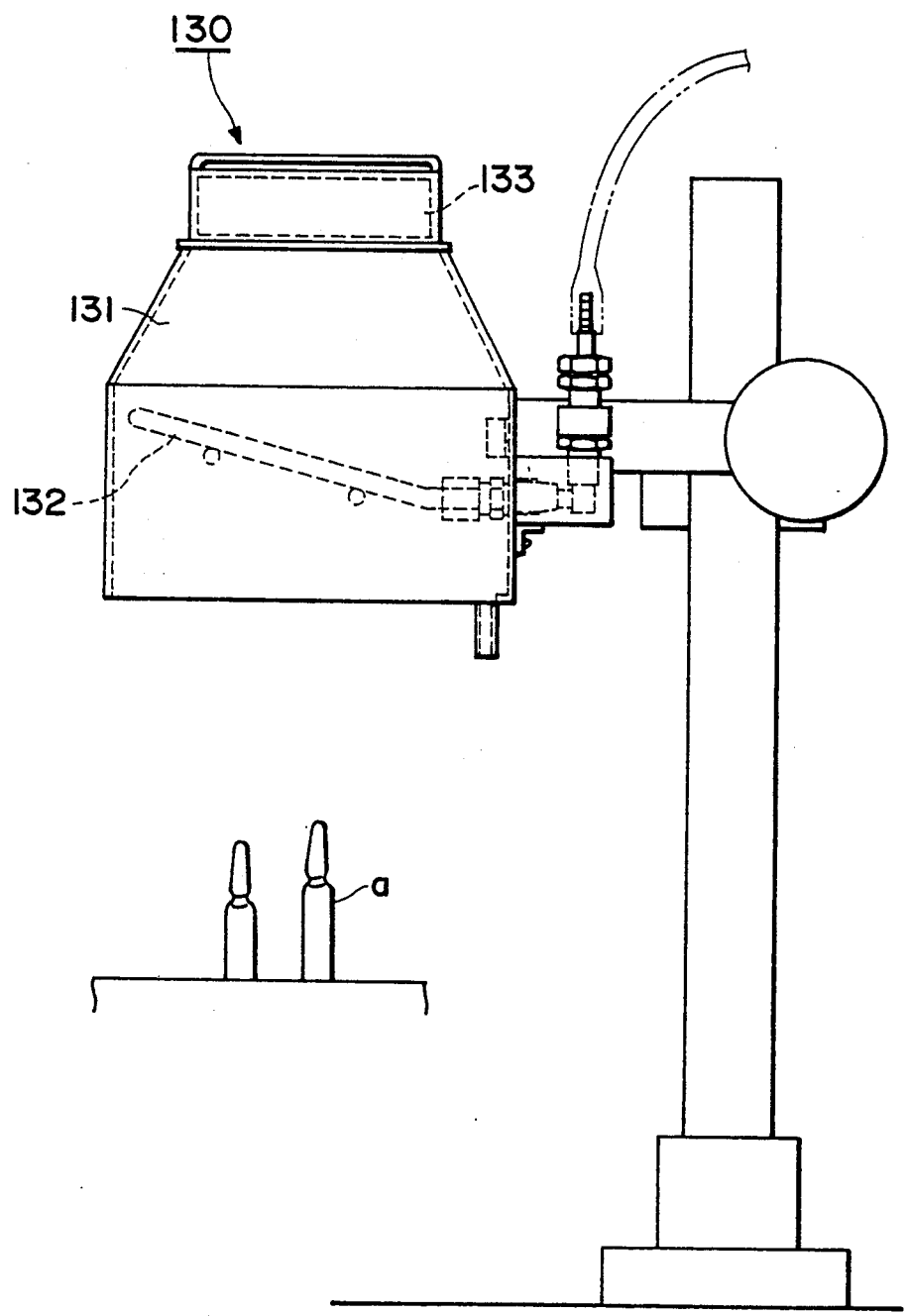
FIG. 15 is a front view of a cooling unit.

Above the screw 23, there is provided a cooling unit 130 as shown in FIG. 15.

Figure 16A:
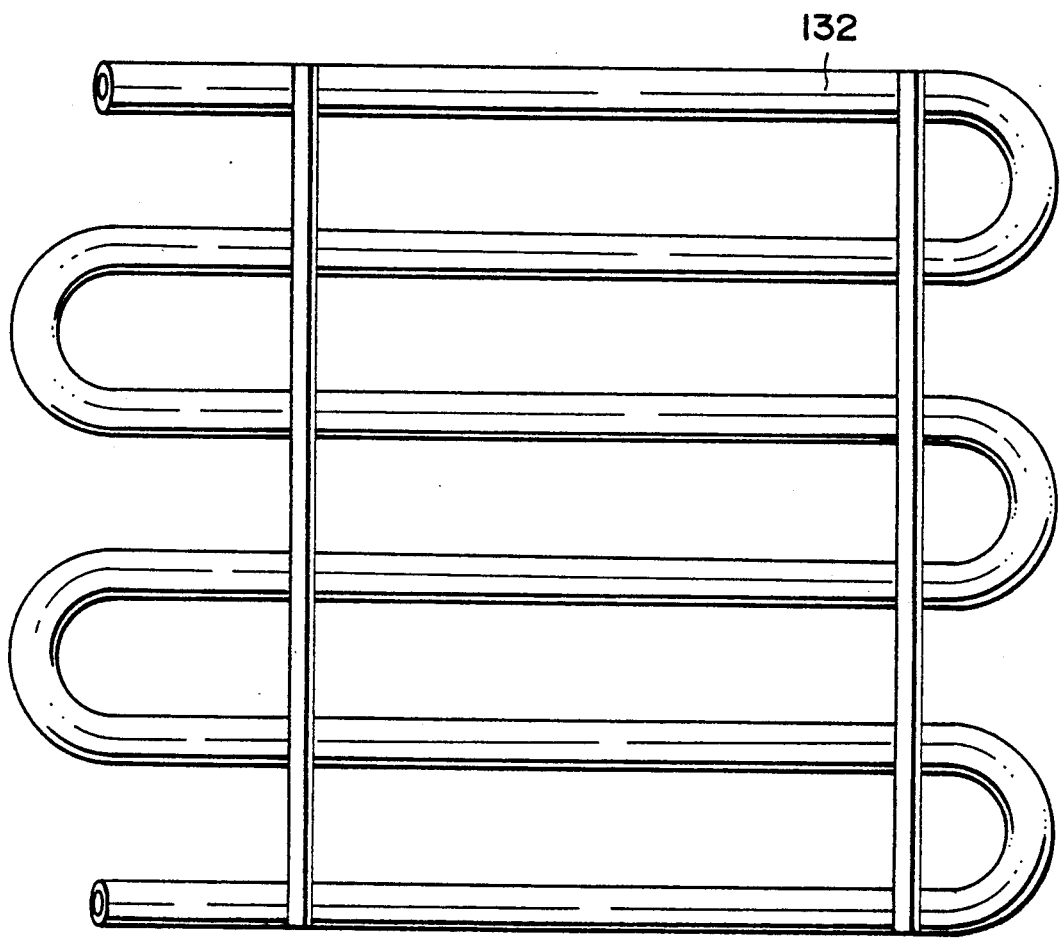
FIGS. 16A and 16B are plan and front views, respectively, of a radiator.
Figure 16B:
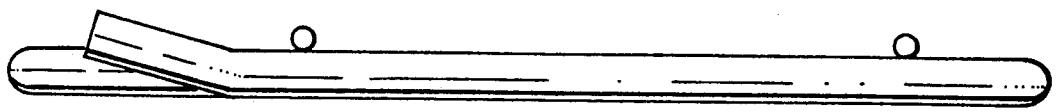

A hood 131 of this cooling unit 130 includes therein a radiator pipe 132 as shown in FIGS. 16A, B and an air stream supplied from a fan 133 rotating above said radiator pipe 132 is cooled by the latter so that a cooled air blast may be supplied to the ampules (a) on the outlet 25 for acceptable products in order to cool these ampules (a) having been heated in the sterilizer 10.

Operation of the sterilizer constructed according to the invention as has been described hereinabove may be summarized as follows:

The hopper 12 provided with the feed fail-safe mechanism 120 continuously feeds the ampules (a) to the conveyor bucket 14 without any feed vacancy and said conveyor bucket 14 holds and coneys these ampules (a) to the sterilizer 10.

The ampules (a) pass first through the preheating station 50 with the heads (ah) and the intermediate portions of the ampules (a) being preponderantly preheated.

The ampules (a) having left the preheating station 50 now pass through the heating station 70 wherein the ampules (a) are irradiated on their lower portions (aL) with microwave as they travel through the irradiator furnace 71. Thus medical fluid contained in each ampule (a) absorbs the microwave energy and is sufficiently heated to be sterilized.

Since the ampules (a) go ahead against the direction of microwave irradiation, the microwave energy to which the ampules (a) are exposed increases as the ampules () go ahead int he irradiator furnace 71, so it is assured that the ampules (a) are gradually heated up to the peak temperature attained by them at the outlet 71b of the irradiator furnace 71.

Before the ampules (a) are lifted up by the slope portion 40s of the rail 40, the ampules (a) are heated primarily on their portions slightly lower than the middle level resulting in conventionally heating the quantity of medical fluid occupying the portion of each ampule (a) higher than said middle level as the ampules (a) travel along the first half 40a of the rail 40 defined with respect to said slope portion 40s and then the ampules (a) are heated primarily on their bottom portions as they travel along the second half 40b of the rail 40 also defined with respect to said slope portion 40s, so that a vertical difference in a temperature of entire medical fluid contained in each ampule (a) is effectively minimized.

Since the following ampules (a) also are sufficiently irradiated with microwave as previously pointed out, it is assured thereby that the ampules (a) are gradually heated as they travel from the inlet 71a to the outlet 71b of the irradiator furnace 71.

Since the feed fail-safe mechanism 120 provided in associated with the hopper 12 assures that the ampules (a) are continuously fed to the sterilizer 10 without any feed vacancy, the undesirable situation can be avoided, in which the ampules (a) held in the conveyor bucket before and after a toothless location, i.e., ampule-free location possibly occurring along the conveyor bucket would be irradiated with harmfully excessive microwave, and the respective ampules (a) are irradiated with constant microwave energy.

As the same time, the ampule heads (ah) are heated by the hot air heaters 93a, 93b in the hot air case 72 and the hot air heater 93b provided on the outlet 71b heats them up to a predetermined peak temperature required for effective sterilization.

The ampules (a) thus heated up to the predetermined temperature for sterilization travel through the passage without loss of said temperature and then conveyed by the conveyor bucket 14 into the thermostatic station 110 in which the ampules (a) are maintained by the heaters 113, 114 at said temperature required for sterilization to achieve a reliable sterilization.

The ampules (a) having been sterilized by traveling through the preheating station 50, the heating station 70 and the thermostatic station 110 are then taken by the discharging star wheel 22 out from the conveyor bucket 14 and transported by the screw 23 onto the sorting guide 24.

The sorting guide 24 selectively transfers the ampules (a) onto the outlet for acceptable products 25 and onto the outlet for unacceptable products 26. The ampules (a) sorted onto the outlet for acceptable products 25 are cooled by the cooling unit 130.

EXAMPLE 1

To verify the effect of the invention as has been described above, the inventors conducted a series of experiments. Result of the experiment conducted by the inventors on the heating behavior of the sterilizer 10 is shown in TABLES 1 and 2.

In the experiment, the inventors used medical fluid as follows:
For experiment 1 NaCl solution
For experiment 2 Theophylline

TABLE 1

Result of heating experiment

| Medicine | NaCl(ag) 2 ml |
|---|---|
| Microwave output | 4700 W |
| Total number of ampules | 458 |
| Number of acceptable products | 485 (100%) |
| Number of unacceptable products | 0 (0%) |
| Preset temperature range for acceptable products | 138.0–155.0° C. |
| Average value (for upper fluid portion) | 144.4° C. |
| Average value (for lower fluid portion) | 143.6° C. |

TABLE 1-continued

Result of heating experiment

| Max. value (for upper fluid portion) | 148.9° C. |
|---|---|
| Max. value (for lower fluid portion) | 149.0° C. |
| Min. value (for upper fluid portion) | 138.9° C. |
| Min. value (for lower fluid portion) | 138.4° C. |

TABLE 2

Result of heating experiment

| Medicine | Theophylline 2 ml |
|---|---|
| Microwave output | 4700 W |
| Total number of ampules | 1064 |
| Number of acceptable products | 1064 (100%) |
| Number of unacceptable products | 0 (0%) |
| Preset temperature range for acceptable products | 138.0–155.0° C. |
| Average value (for upper fluid portion) | 144.6° C. |
| Average value (for lower fluid portion) | 144.7° C. |
| Max. value (for upper fluid portion) | 148.4° C. |
| Max. value (for lower fluid portion) | 148.9° C. |
| Min. value (for upper fluid portion) | 140.5° C. |
| Min. value (for lower fluid portion) | 141.2° C. |

EXAMPLE 2

Result of comparative experiment conducted on the sterilizing effect achieved by the sterilizer 10 of the invention and the conventional auto clave is shown by TABLE 3.

The sterilizing experiment was conducted under conditions as follow:

(1) Indicator bacilli:
   Bacillus stearothermophilus ATcc
   7953 spore fluid (thermostable bacillus)
(2) Thermostability of the indicator bacillus:
   D 121 value=4 min.
(3) Disperse medium:
   PBS (0.2 M phosphate buffer, 0.85% physiological saline, pH 7.2)
(4) Initial number of bacilli:
   $2.8 \times 10^6$
(5) Ampule size:
   1 ml

TABLE 3

Result of sterilizing test

| Product temperature | Sterilizer (A) Number of survival bacilli | Auto clave Sterilizing condition | Number of survival bacilli |
|---|---|---|---|
| 135° C. | $5.2 \times 10^3$ | 121° C. × 6 min | $5.7 \times 10^2$ |
| 140° C. | $1.6 \times 10^2$ | 121° C. × 8 min | $2.3 \times 10^2$ |
| 145° C. | 0 | 121° C. × 12 min | 40 |
| 150° C. | 0 | 121° C. × 20 min | 0 |

The result shown in the above TABLE indicates that the sterilizer 10 of the invention is substantially higher in its sterilizing effect and the survival bacilli are correspondingly fewer than achieved by the conventional auto clave.

The sterilizer 10 of the invention demonstrated the sterilizing effect far beyond the sterility levels prescribed in accordance with both the general testing procedures of the Japanese Pharmacopoeia and the PDA (Society of Injection Medicine in USA).

The sterilizing effect of the sterilizer 10 well achieves F0 value of 12 which is the indicator level for the PDA sterility level.

While the invention has been particularly shown and described with reference to preferred embodiment thereof, it will be understood by those skilled in the art that the foregoing and other changes in form and details can be made therein without departing from the sprit and scope of the invention.

What is claimed is:

1. An apparatus for sterilizing a sealed container utilizing microwaves, comprising an a irradiator furnace provided through its top wall with a slot and connected to a square waveguide functioning to propagate microwaves into the furnace, a conveyor bucket adapted to hold respective sealed containers in a generally vertical direction with their lower portions inserted through said slot into the irradiator furnace and to convey the respective sealed containers along said slot and a rail with a top portion thereof extending from a lower level at the furnace inlet to a higher level at the furnace outlet, said rail serving to slidably support the bottom of each sealed container and with the bucket orient the container in a generally vertical direction while passing through said furnace.

2. An apparatus for sterilizing a sealed container utilizing microwaves as recited in claim 1, wherein said rail supporting the bottom of each sealed container is stepped.

3. An apparatus for sterilizing a sealed container utilizing microwaves as recited in claim 1, wherein there is provided in a floor of said irradiator furnace a cavity-like groove in which said rail for supporting the bottom of each sealed container is securely received.

4. An apparatus for sterilizing a sealed container utilizing microwaves as recited in claim 1, wherein there is provided in the irradiator furnace at the outlet thereof a notch, and a means for measuring the temperature of the sealed container is located near said notch.

5. An apparatus for sterilizing a sealed container utilizing microwaves as recited in claim 1, wherein a passage extending from the outlet of the furnace is provided with a width substantially as same as the width of the slot.

6. An apparatus for sterilizing a sealed container utilizing microwaves as recited in claim 1, further comprising means for vertically moving a portion of these irradiator furnace.

7. An apparatus for sterilizing a sealed container utilizing microwave as recited in claim 1, further comprising a hot air case provided above the irradiator furnace.

8. An apparatus for sterilizing a sealed container utilizing microwaves, comprising an irradiator furnace provided through its top wall with a slot and connected to a square waveguide functioning to propagate microwaves, a conveyor bucket adapted to hold respective sealed containers with their lower portions inserted through said slot into the irradiator furnace and to convey the respective sealed containers along said slot in a generally vertical direction, and an IR heater adapted for thermostatically heating the sealed containers conveyed out from the irradiator furnace.

9. An apparatus for sterilizing a sealed container utilizing microwaves, including an irradiator furnace provided through its top wall with a slot and connected to a square waveguide functioning to propagate microwaves and a conveyor bucket adapted to hold the respective sealed containers in a generally vertical direction and having their lower portions inserted through said slot into the irradiator furnace and to convey the respective sealed containers along said slot, said apparatus being characterized by that there is provided at an outlet of said furnace an extended passageway.

10. An apparatus for sterilizing a sealed container utilizing microwaves as recited in claim 9, wherein the width of said passageway is same as the slot.

11. An apparatus for sterilizing a sealed container utilizing microwaves as recited in claim 9, wherein said passageway is provided with a thermostatic station in which an IR heater thermostatically heats the sealed container.

12. An apparatus for sterilizing a sealed container utilizing microwaves, comprising an irradiator furnace provided through its top wall with a slot and connected to a square waveguide functioning to propagate microwaves, a conveyor bucket adapted to hold the respective sealed containers with their lower portions inserted through said slot into the irradiator furnace and to convey the respective sealed containers along said slot, a conveyor belt adapted to convey the sealed containers to grooves of a screw and the screw is rotatable to convey said sealed containers feeding star wheel adapted to feed the sealed containers the conveyor bucket, a sensor adapted to detect whether an individual screw groove is loaded with a sealed container or not and auxiliary feeding guides adapted feed a sealed container into an empty groove when said sensor detects that an individual screw groove is not loaded with a sealed container.

* * * * *